(12) United States Patent
Kamei et al.

(10) Patent No.: US 7,862,895 B2
(45) Date of Patent: Jan. 4, 2011

(54) ORGANOPOLYSILOXANE COMBINATION FOR SURFACE TREATMENT, POWDER TREATED WITH THE COMBINATION, AND COSMETIC COMPRISING THE POWDER

(75) Inventors: Masanao Kamei, Annaka (JP); Akira Yamamoto, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 1078 days.

(21) Appl. No.: 11/528,451

(22) Filed: Sep. 28, 2006

(65) Prior Publication Data

US 2007/0071980 A1    Mar. 29, 2007

(30) Foreign Application Priority Data

Sep. 28, 2005 (JP) ............... 2005-282920
Sep. 25, 2006 (JP) ............... 2006-258265

(51) Int. Cl.
  *B32B 9/00*   (2006.01)
(52) U.S. Cl. .................. 428/405; 424/401; 424/490; 424/497; 424/70.12
(58) Field of Classification Search ............ 424/401, 424/490, 497, 70.12; 428/405
  See application file for complete search history.

(56) References Cited

U.S. PATENT DOCUMENTS

| | | | |
|---|---|---|---|
| 5,368,639 A * | 11/1994 | Hasegawa et al. ......... 106/490 |
| 6,660,281 B1 | 12/2003 | Nakanishi et al. |
| 7,338,995 B2 * | 3/2008 | May et al. ................. 524/205 |
| 2004/0091439 A1 | 5/2004 | Kamei et al. |
| 2004/0156809 A1 * | 8/2004 | Ono et al. ................ 424/70.12 |
| 2006/0165629 A1 | 7/2006 | Kamei et al. |

FOREIGN PATENT DOCUMENTS

| EP | 1065234 A2 | 1/2001 |
|---|---|---|
| EP | 1 405 624 A1 | 4/2004 |
| EP | 1416016 A1 | 5/2004 |
| JP | 06-116120 A | 4/1994 |
| JP | 7-053326 A | 2/1995 |
| JP | 07-053326 A | 2/1995 |
| JP | 07-196946 A | 8/1995 |
| JP | 7-196946 A | 8/1995 |
| JP | 2719303 B2 | 11/1997 |
| JP | 2001-72891 A | 3/2001 |
| JP | 2004-231609 A | 8/2004 |
| WO | WO-02/100356 A1 | 12/2002 |

OTHER PUBLICATIONS

Abstract JP 02-029420 Jan. 31, 1990.*

* cited by examiner

*Primary Examiner*—Margaret G Moore
(74) *Attorney, Agent, or Firm*—Birch, Stewart, Kolasch & Birch, LLP

(57) ABSTRACT

A combination of for surface treating powder is disclosed. The combination comprises a mixture of an organopolysiloxane (I) and organopolysiloxane (II), a mixture of an organopolysiloxane (I) and acryl/silicone copolymer (III) or a mixture of an organopolysiloxane (I), organopolysiloxane (II) and acryl/silicone copolymer (III) as defined herein. The organopolysiloxane (I) is represented by the following formula (1)

$$R^1_a(OR^2)_b SiO_{(4-a-b)/2}$$

with the subscripts "a" and "b" and groups $R^1$ and $R^2$ defined herein. The organopolysiloxane (II) is represented by the formula $$R^3_c R^4_d R^5_e SiO_{(4-c-d-e)/2}$$

with the subscripts "c", "d" and "e" defined and groups $R^3$ and $R^4$ defined herein, and group $R^5$ being a silicone compound residue of the formula

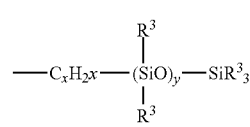

(3)

as defined herein.

29 Claims, No Drawings

ORGANOPOLYSILOXANE COMBINATION FOR SURFACE TREATMENT, POWDER TREATED WITH THE COMBINATION, AND COSMETIC COMPRISING THE POWDER

This application claims benefits of Japanese Patent application No. 2005-282920 filed on Sep. 28, 2005, and 2006-258265 filed on Sep. 25, 2006, the contents of which are hereby incorporated by reference.

FIELD OF THE INVENTION

The present invention relates to organopolysiloxane a combination for surface treating powder, powder treated with the combination and a cosmetic comprising the powder. The combination is composed of at least two organopolysiloxanes having different functions. The treated powder has excellent water resistance, and stability with time. The cosmetic comprising the powder has good affinity to the skin or hair and lasts long on the skin or hair.

DESCRIPTION OF THE PRIOR ART

Generally, human secretions such as sweat, tears and sebum cause makeup runs. Particularly, sunscreen agents and makeup cosmetics, an oil agent contained in cosmetics along with sebum secreted from the skin causes excessive wetting of cosmetic powder, which results in serious makeup runs. In order to reduce the amount of the oil agent, use is made of a volatile oil such as octamethylcyclotetrasiloxane or decamethylcyclopentasiloxane.

Friction and Water is also an external factor causing the makeup runs. In order to prevent the makeup runs caused by water-soluble substances such as sweat and tear, silicone oil, which is highly water repellent, is added to cosmetics. For example, dimethylpolysiloxane is widely used in cosmetics because of its superior features such as light to the touch, excellent water repellency, and high safety. Meanwhile, pigments such as titanium oxide, zinc oxide, and iron oxide red and powder such as mica and sericite are widely used in cosmetics, for example, sunscreen agent, nail color, nail coat, foundation, mascara, and eyeliner. The powder is generally treated with alumina, silica, oils, metal soaps, and organosiloxane to be resistance to water and sebum.

As an organopolysiloxane for treating powder, the one having reactive sites is used. These reactive sites form chemical bonds with reactive groups in powder. Consequently, the organopolysiloxane is not released from the powder when the treated powder is incorporated in cosmetics containing solvents.

As an example of the organopolysiloxane, methylhydrogenpolysiloxane-type treatment agent is known from Japanese patent No. 2719303. The methylhydrogenpolysiloxane-type treatment agent, such as methylhydrogenpolysiloxane and dimethylhydrogenpolysiloxane provide good resistance to water. However, when unreacted Si—H bonds remain on powder, they may react with an ingredient in cosmetic to evolve hydrogen gas. Japanese Patent Application Laid-Open No. 7-196946 discloses a linear silicone modified to have an alkoxy group at one end. However, the alkoxy-modified silicone has a few sites which is reactive to powder, so that the powder surface tends to remain untreated, resulting in unsatisfactory improvement in water resistance. In addition, Japanese Patent Application Laid-Open No. 2001-72891 describes a branched silicone having a hydrolyzable group and WO02/100356 describes an acryl/silicone copolymer having a hydrolyzable group. These surface-treatment agents provide softness to the touch and affinity to the skin to powder. However, deactivation of powder surface and improvement of water resistance by these surface-treatment agents are not satisfactory.

SUMMARY OF THE INVENTION

An object of the present invention is to provide surface treatment composition which provides powder with good affinity to the skin or hair and does not form hydrogen gas.

Another object of the present invention is to provide powder treated with the composition and cosmetics containing the powder.

The present invention is a combination for surface treating powder, composed of (I) organopolysiloxane or condensate thereof and (II) organopolysiloxane in a weight ratio of (I):(II) of from 95:5 to 5:95;

(I) organopolysiloxane or condensate thereof and (III) acryl/silicone copolymer in a weight ratio of (I):(III) of from 95:5 to 5:95; or (I) organopolysiloxane or condensate thereof, (II) organopolysiloxane and (III) acryl/silicone copolymer in a weight ratio of (I):[(II)+(III)] of from 95:5 to 5:95, provided that each of (I), (II), and (III) may be packed together or separately, wherein (I) organopolysiloxane is represented by the following formula (1),

wherein $R^1$ may be the same with or different from each other and is a $C_{1-30}$ alkyl, aryl, aralkyl, fluorinated alkyl or amino-substituted alkyl group, R2 is a $C_{1-6}$ alkyl group, a is the number of from 0.75 to 1.5, and b is the number of from 0.2 to 3, provided that a sum of a and b is greater than 0.9 and at most 4;

(II) organopolysiloxane is represented by the formula (2)

wherein $R^3$ may be the same with or different from each other and is a $C_{1-30}$ alkyl, aryl, aralkyl, or fluorinated alkyl group, $R^4$ is a hydrogen atom, a hydroxyl group or a $C_{1-6}$ alkoxy group and is bonded to the Si atom in the formula (2) via a group comprising carbon, oxygen, or silicon atom, and $R^5$ is a silicone compound residue represented by the following formula

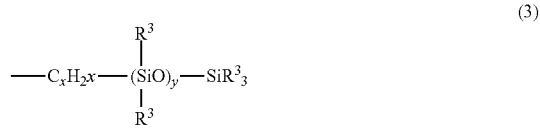

wherein R3 is as defined above, c is the number of from 1.0 to 2.5, d is the number of from 0.001 to 1.5, and e is the number of from 0 to 1.5, x is an integer of from 1 to 5, and y is an integer of from 0 to 500; and (III) acryl/silicone copolymer has at least one hydrolyzable silyl group.

The above organopolysiloxane combination of the present invention can attain synergistic effects of components, which effect cannot be attained by merely mixing powder treated with individual component. The treated powder is resistant to sweat and adheres well to the skin. Further, there is no danger for evolving hydrogen gas.

DESCRIPTION OF THE PREFERRED EMBODIMENTS

In the present invention, any powder which are commonly used in cosmetics may be used, regardless of the shape such as spherical, spindle forms, acicular, and plate-like; particle size such as fume size, fine particles and pigment grade; and particle structure such as porous and non-porous. Examples of the powder include inorganic powder, organic powder, metal salt powder of surface active agent, colored pigments, pearl pigments, metallic powder pigments, and natural colors and the like.

Examples of the inorganic powder include titanium oxide, zirconium oxide, zinc oxide, cerium oxide, magnesium oxide, barium sulfate, calcium sulfate, magnesium sulfate, calcium carbonate, magnesium carbonate, talc, mica, kaolin, sericite, muscovite, synthetic mica, phlogopite, lepidolite, biotite, lithia mica, silicic acid, silicic anhydride, aluminum silicate, magnesium silicate, aluminum magnesium silicate, calcium silicate, barium silicate, strontium silicate, metal salts of tungstenic acid, hydroxyapatite, vermiculite, higilite, bentonite, montmorillonite, hectoliter, zeolite, ceramics powder, calcium secondary phosphate, alumina, aluminum hydroxide, boron nitride, among which zinc oxide, titanium oxide, mica, sericite, talc, and kaolin are preferred.

Examples of the organic powder include polyamide powder, polyester powder, polyethylene powder, polypropylene powder, polystyrene powder, styrene/acrylic acid copolymer, divinylbenzene/styrene copolymer, polyurethane powder, urea resin, melamine resin, polymethylbenzoguanamine powder, tetrafluoroethylene, polymethylmethacrylate, nylon powder, phenol resin, epoxy resin, and polycarbonate resin; natural polymers such as cellulose, starch powder, silk powder, and microcrystalline fiber powder; silicones such as crosslinked dimethylsilicone, polymethylsilsesquioxane, spherical silicone gum coated with polymethylsilsesquioxane particles, silicone gum, and lipophylized silica powder; and low-molecular weight compound such as lauroyl lysine and benzoguanamine powder.

Examples of metal salt of surface active agent (metal soaps) include zinc stearate, aluminum stearate, calcium stearate, magnesium stearate, zinc myristate, magnesium myristate, zinc cetyl phosphate, calcium cetyl phosphate, and zinc/sodium cetyl phosphate.

Examples of colored pigments include inorganic red pigments such as iron oxide, iron hydroxide, and iron titanate, inorganic brown pigments such as γ-iron oxide, inorganic yellow pigments such as iron oxide yellow and loess, inorganic black pigments such as iron oxide black and carbon black, inorganic violet pigments such as manganese violet and cobalt violet, inorganic green pigments such as chromium hydroxide, chromium oxide, cobalt oxide, and cobalt titanate, inorganic blue pigments such as Prussian blue and ultramarine blue, lakes of tar pigments, lakes of natural dyes, and synthetic resin powder complexes thereof.

Examples of the pearl pigments include titanium oxide-coated mica, titanium oxide-coated mica, bismuth oxychloride, titanium oxide-coated bismuth oxychloride, titanium oxide-coated talc, fish scales, and titanium oxide-coated colored mica; metallic powder pigments such as aluminum powder, copper powder and stainless powder.

Examples of the tar pigments include Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, and Orange No. 207; and natural pigments such as carminic acid, laccaic acid, carthamin, brazilin, and crocin.

The present combination for surface treatment is composed of
(I) organopolysiloxane or condensate thereof and (II) organopolysiloxane;
(I) organopolysiloxane or condensate thereof and (III) acryl/silicone copolymer; or
(I) organopolysiloxane or condensate thereof, (II) organopolysiloxane and (III) acryl/silicone copolymer.

The organopolysiloxane (I) is represented by the following formula (1)

$$R^1_a(OR^2)_b SiO_{(4-a-b)/2} \tag{1}$$

wherein $R^1$ is an alkyl, aryl, aralkyl, fluorinated alkyl or amino-substituted alkyl group each having 1 to 30 carbon atoms, which may be different from each other when a plurality of $R^{1'}$ is present per molecule. Examples of the $R^1$ include alkyl groups such as methyl, ethyl, propyl, butyl, pentyl, hexyl, heptyl, octyl, nonyl, decyl, lauryl, cetyl, stearyl and behenyl groups; cycloalkyl groups such as cyclopentyl and cyclohexyl groups; aryl groups such as phenyl and tolyl groups; aralkyl groups such as benzyl and phenetyl groups; fluorinated alkyl groups such as trifluoropropyl and heptadecafluorodecyl groups; amino-substituted alkyl group such as aminopropyl group, among which methyl, phenyl and aminopropyl groups are preferred.

$R^2$ is an alkyl group having 1 to 6 carbon atoms such as methyl, ethyl or isopropyl group, preferably methyl or ethyl group. The number, a, is of from 0.75 to 1.5, and b is of from 0.2 to 3, provided that the sum of a and b, i.e., a+b, is greater than 0.9 and at most 4.

The organopolysiloxane (I) may be in the form of a condensate of the organopolysiloxane of the formula (1). The condensate may be prepared by heating the organopolysiloxane to such a temperature that $OR^2$ in the formula (1) is hydrolyzed. The condensate preferably has a molecular weight, reduced to polystyrene, of from 300 to 5000.

The organopolysiloxane (II) is represented by the formula (2)

$$R^3_c R^4_d R^5_e SiO_{(4-c-d-e)/2} \tag{2}$$

wherein $R^3$ is an alkyl, aryl, aralkyl, or fluorinated alkyl group each having 1 to 30 carbon atoms, which may be different from each other when a plurality of $R^{3'}$ is present. Examples of the $R^3$ include alkyl groups such as methyl, ethyl, propyl, butyl, pentyl, hexyl, heptyl, octyl, nonyl, decyl, lauryl, cetyl, stearyl and behenyl groups; cycloalkyl groups such as cyclopentyl and cyclohexyl groups; aryl groups such as phenyl and tolyl groups; aralkyl groups such as benzyl and phenetyl groups; and fluorinated alkyl groups such as trifluoropropyl and heptadecafluorodecyl groups, among which methyl and phenyl groups are preferred.

$R^4$ is a group selected from the group consisting of a hydrogen atom, a hydroxyl group and an alkoxy group having 1 to 6 carbon atoms such as methoxy, ethoxy, or isopropoxy group. Preferably, $R^4$ is hydroxyl or ethoxy group. $R^4$ may be bonded Si atom in the formula (2) via a group comprising a carbon, oxygen, or Si atom, for example, dimetylethoxysilyl group. Moreover, $R^4$ may be multifunctional group such as diethoxymethylsilyl or triethoxysilyl group. These groups can be introduced to the organopolysiloxane by adding vinyltrichlorosilane, vinyltris(β-methoxy)silane, vinyltrimetoxysilane, or vinyltriethoxysilane to an organosiloxane having an SiH group.

$R^5$ is a silicone compound residue represented by the following formula (3)

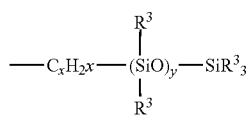
(3)

wherein $R^3$ is as defined above, x is an integer of from 1 to 5, preferably from 2 to 4, and y is an integer of from 0 to 500, preferably from 0 to 100.

In the formula (2), c is the number of from 1.0 to 2.5, d is the number of from 0.001 to 1.5, and e is the number of from 0 to 1.5.

In addition to the aforesaid organopolysiloxane (I) and (II), or in place of (II), use of (III) acryl/silicone copolymer having at least one hydrolyzable silyl group per molecule will improve affinity or adhesion of the powder to the skin.

The acryl/silicone copolymer has the following repeating units of (a), (b) and (c).

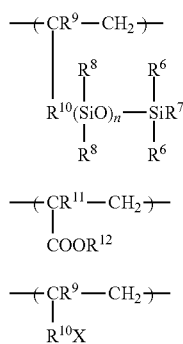
(a)

(b)

(c)

In the repeating units (a), (b) and (c), each of $R^6$-$R^8$, which may be the same with or different from each other, is selected from the group consisting of alkyl groups, aryl groups, aralkyl groups and fluorinated alkyl groups, each having 1 to 30 carbon atoms, each of $R^9$ and $R^{11}$, which may be the same with or different from each other, is selected from the group consisting of a hydrogen atom and a methyl group, $R^{10}$, which may be the same with or different from each other, is an alkyleneoxycarbonyl group having 2 to 11 carbon atoms or a phenylene group, $R^{12}$ is an alkyl group having 1 to 30 carbon atoms, X is the hydrolyzable silyl group as described above, and n is an integer of from 3 to 500.

Preferred hydrolyzable silyl group has a —Si—O— moiety, for example, an alkoxysilyl group or acetoxysilyl group. More preferred silyl group is represented by the formula:

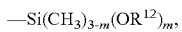

wherein $R^{12}$ is an alkyl, alicyclic, alkenyl, aryl, or aralkyl group, preferably an alkyl or alkenyl group having 1 to 4 carbon atoms. Most preferably, R is an ethyl group. In the above formula, m is an integer of from 1 to 3. When m is 2 or 3, a plurality of R's may be different from each other.

Example of preferred hydrolyzable silyl group include dimethylethoxysilyl group, methyldiethoxysilyl group and triethoxysilyl group, among which triethoxysilyl group is particularly preferred.

The acryl/silicone copolymer can be prepared by reacting an acrylic polymer with an organopolysiloxane. For example, it can be prepared by copolymerizing an organopolysiloxane represented by the following formula (4) having a radically polymerizable group, an acrylic monomer represented by the following formula (5), and a silane compound represented by the following formula (6) having a radically polymerizable group.

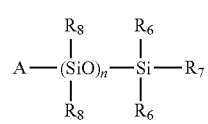
(4)

wherein $R^6$ to $R^8$ and n are as defined above, A is a radically polymerizable group represented by the following formula (7)

$$CH_2=C(R^4)R^5—\qquad(7)$$

wherein $R^9$ and $R^{10}$ are as defined above,

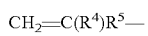
(5)

wherein $R^6$ and $R^{12}$ are as defined above,

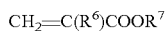
(6)

wherein B is selected, independently of A, from the groups defined for A above, X is the aforesaid hydrolyzable silyl group, preferably the following group

wherein $R^{13}$ and m are as defined above, and $R^{12}$'s may be different from each other when m is 2 or 3.

The organopolysiloxane compound represented by the formula (6) having a radically polymerizable group is called a silicone macromonomer. It has the radically polymerizable group at one end only. From the compound, the repeating unit (1) can be derived.

In the formula (4), examples of A include (meth)acryloxymethyl group, (meth)acryloxypropyl group, (meth)acryloxydecyl group, styryl group, and α-methylstyryl group, among which a (meth)acryloxypropyl group is preferred.

In the formulae (a) and (4), examples of $R^6$ include alkyl groups such as methyl, ethyl, propyl, butyl, pentyl, hexyl, heptyl, octyl, nonyl, decyl and cyclohexyl groups; aryl groups such as phenyl and tolyl groups; aralkyl groups such as benzyl and phenetyl groups; and fluorinated alkyl groups such as trifluoropropyl and nonafluorobutylethyl groups. Preferably, most of $R^1$ are methyl groups because of good feel to the touch.

In the formulae (a) and (4), n is an integer of from 3 to 500, preferably from 9 to 200. An acryl/silicone copolymer with n less than the aforesaid lower limit may not provide satisfactory conditioning effect. An organopolysiloxane compound with n above the aforesaid upper limit may not copolymerize with the acrylic monomer or the radically polymerizable silane compound with ease to make it difficult to obtain a desired copolymer.

From the acrylic monomer of the formula (5), the repeating unit (b) can be derived. Examples of the monomer include methyl (meth)acrylate, ethyl (meth)acrylate, isopropyl (meth)acrylate, n-butyl (meth)acrylate, tert-butyl (meth)

acrylate, cyclohexyl (meth)acrylate, 2-ethylhexyl (meth) acrylate, tridecyl (meth)acrylate, stearyl (meth)acrylate, isostearyl (meth)acrylate, behenyl (meth)acrylate, and a combination thereof. Preferably, used is made of methyl (meth)acrylate or a combination of any one of the aforesaid monomers which can give a homopolymer having a higher glass transition temperature (Tg), and another monomer of the aforesaid monomers which gives a homopolymer having a low Tg.

From the radically polymerizable silane compound of the formula (6), the aforesaid repeating unit (c) can be derived. Examples of the silane compound include γ-methacryloxypropyl-trimethoxysilane, γ-methacryloxypropyl-methyldimethoxysilane, γ-methacryloxypropyl-dimethylmethoxysilane, γ-methacryloxypropyl-triethoxysilane, γ-methacryloxypropyl-methyldiethoxysilane, γ-methacryloxypropyl-tributhoxysilane, γ-methacryloxypropyl-isopropenoxysilane, γ-acryloxypropyl-trimethoxysilane, γ-acryloxymethyl-trimethoxysilane, γ-acryloxypropyl-triethoxysilane, γ-acryloxypropylmethyl-diethoxysilane, styryltrimethoxysilane, styryltriethoxysilane, α-methylstyryltrimethoxysilane, and a mixture thereof. Preferably, γ-methacryloxypropyl-triethoxysilane is used.

A ratio of the monomers of the formulas (4), (5) and (6) is such that the organopolysiloxane compound of the formula (4) having a radically polymerizable group is in an amount of from 1 to 97 wt %, preferably from 5 to 90 wt %, the acrylic monomer of the formula (5) is in an amount of from 0 to 95 wt %, preferably from 2 to 60 wt %, and the radically polymerizable silane compound of the formula (6) is in an amount of from 1 to 10 wt %, preferably from 2 to 7 wt %, based on a total weight of the monomers.

The organopolysiloxane (I), the organopolysiloxane (II), and the acryl/silicone copolymer (III) have a weight average molecular weight, reduced to polystyrene, of preferably from 300 to 100,000, particularly from 500 to 50,000. Generally, an organosiloxane compound having a molecular weight greater than 100,000 is too viscous and powder treated with such an organosiloxane tend to give a cosmetic which is not so comfortable to use. On the other hand, an organosiloxane having a molecular weight less than 300 lacks softness to the touch, which is inherent to an organosiloxane having larger molecular weight.

In the present combination, an amount of each component (I), (II), and (III) is preferably adjusted according to chemical composition and surface area of the powder. Too little amount of each component may result in insufficient improving in water resistance or touch of the powder, and too much content may result in worse touch or coagulation of the powder. Typically, each component is used in an amount, per 100 parts by weight of the powder, of from 0.05 to 20 parts by weight, preferably from 0.5 to 5 parts by weight. The ratio of each component, i.e., (I):(II), (I):(III), or (I):(II)+(III), is preferably of from 95:5 to 5:95, more preferably from 80:20 to 20:80, most preferably from 70:30 to 30:70. In the combination of (I), (II) and (III), the weight ratio of (II):(III) is preferably of from 95:5 to 5:95, more preferably from 80:20 to 20:80, most preferably from 70:30 to 30:70.

In the present combination, components (I), (II) and (III) may be packed together as a composition. Alternatively, they may be separately as a set or package of two or three components. That is, the powder surface can be treated simultaneously or sequentially with (I), (II) and (III). Surface treatment may be performed preferably by mixing all the components used and then treating powder with the components, but sequential treatment may be more suitable depending on powder to be treated or intended property to be provided. In the sequential treatment, treatment with (I) is performed preferably first, and then treatment with (II) followed by the treatment with (III), or treatment with (II) and (III). Alternatively, treatment with a mixture of (I) and (II), or (I) and (III) may be performed first, and then the treatment with (III) or (II) are performed, respectively. By treating with the aforesaid two or three components, synergistic effect can be attained which effect cannot be attained by merely mixing powder treated with respective components.

The surface treatment can be performed by any known method, for example, the following methods:

1. Dispersing powder to be treated in a solution of the surface treatment combination dissolved in an organic solvent or a dispersion of the treatment combination dispersed in an organic solvent;

2. Mixing powder with the surface treatment combination and subjecting the mixture to a milling apparatus such as a ball mill or jet mill;

3. Dispersing powder to be treated in a solution of the surface treatment combination dissolved in an organic solvent or a dispersion of the surface treatment combination dispersed in an organic solvent, and, after stirring for a predetermined period of time, evaporating the solvent.

The powder treated with the surface treatment combination of the present invention, hereinafter referred to as (A) surface treated powder, can be used for various applications, particularly suitable for cosmetics applied to the skin or hair such as skincare products, makeup products, haircare products, antiperspirants, and UV-ray protective products. An amount of the surface treated powder (A) to be incorporated in a cosmetic, though varies depending on type and form of the cosmetic, ranges from 0.1 to 99 wt % based on a total weight of the cosmetic.

The present cosmetic may contain one or more of (B) unctuous agent according to intended use of the cosmetic. Any oil agents, whether it is solid, semi-solid or liquid, that are commonly used in cosmetics can be used.

Examples of natural plant or animal oils and semi-synthetic oils include avocado oil, linseed oil, almond oil, Ibota wax, perilla oil, olive oil, cacao butter, kapok wax, kayaoil, carnaubawax, Glycyrrhiza oil, candelilla wax, beef tallow, neat's-foot oil, beef bone fat, hydrogenated beef tallow, apricot kernel oil, spermaceti wax, hydrogenated oil, wheat germ oil, sesame oil, rice germ oil, rice bran oil, sugar cane wax, sasanqua oil, safflower oil, shear butter, Chinese tung oil, cinnamon oil, jojoba wax, shellac wax, turtle oil, soybean oil, tea seed oil, camellia oil, evening primrose oil, corn oil, lard, rapeseed oil, Japanese tung oil, rice bran oil, germ oil, horse fat, persic oil, palm oil, palm kernel oil, castor oil, hydrogenated castor oil, castor oil fatty acid methylester, sunflower oil, grape oil, bayberry wax, jojoba oil, macadamia nut oil, beeswax, mink oil, cottonseed oil, cotton wax, Japanese wax, Japanese wax kernel oil, montan wax, coconut oil, hydrogenated coconut oil, tri-coconut oil fatty acid glyceride, mutton tallow, peanut oil, lanolin, liquid lanolin, hydrogenated lanolin, lanolin alcohol, hard lanolin, lanolin acetate, isopropyl lanolate, hexyl laurate, POE lanolin alcohol ether, POE lanolin alcohol acetate, polyethylene glycol lanolate, POE hydrogenated lanolin alcohol ether, and egg yolk oil, wherein POE represents polyoxyethylene.

Examples of hydrocarbon oils include ozokerite, squalane, squalene, ceresin, paraffin, paraffin wax, liquid paraffin, pristane, polyisobutylene, microcrystalline wax, and Vaseline. Examples of higher fatty acids include lauric acid, myristic acid, palmitic acid, stearic acid, behenic acid, undecylenic acid, oleic acid, linoleic acid, linolenic acid, arachidonic acid, eicosapentaenoic acid (EPA), docosahexaenoic acid (DHA), isostearic acid, and 12-hydroxystearic acid.

Examples of the higher alcohols include lauryl alcohol, myristyl alcohol, palmityl alcohol, stearyl alcohol, behenyl alcohol, hexadecyl alcohol, oleyl alcohol, isostearyl alcohol, hexyldodecanol, octyl dodecanol, cetostearyl alcohol, 2-decyltetradecinol, cholesterol, phytosterol, POE cholesterol ether, monostearyl glycerin ether (batyl alcohol), and monooleyl glyceryl ether (cerakyl alcohol).

Examples of ester oils include diisobutyl adipate, 2-hexyldecyl adipate, di-2-heptylundecyl adipate, N-alkyl glycol monoisostearate, isocetyl isostearate, trimethylolpropane triisostearate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, octyldodecyl gum ester, oleyl oleate, octyldodecyl oleate, decyl oleate, isononyl isononanate, neopentyl glycol dicaprirate, triethyl citrate, 2-ethylhexyl succinate, amyl acetate, ethyl acetate, butyl acetate, isocetyl stearate, butyl stearate, diisopropyl sebacinate, di-2-ethylhexyl sebacinate, cetyl lactate, myristyl lactate, isopropyl palmitate, 2-ethylhexyl palmitate, 2-hexyldecyl palmitate, 2-heptylundecyl palmitate, cholesteryl 12-hydroxystearate, dipentaerythritol fatty acid esters, isopropyl myristate, octyldodecyl myristate, 2-hexyldecyl myristate, myristyl myristate, hexyldecyl dimethyloctanoate, ethyl laurate, hexyl laurate, 2-octyldodecyl N-lauroyl-L-glutamate, and diisostearyl. Examples of glyceride oils include acetoglyceryl, glycerol triisooctanoate, glyceryl triisostearate, glyceryl triisopalmitate, glyceryl monostearate, glyceryl di-2-heptylundecanoate, glyceryl trimyristate, and diglyceryl myristyl isostearate.

Examples of silicone oils include linear organopolysiloxanes having a low viscosity to a high viscosity, such as dimethylpolysiloxane, methylphenylpolysiloxane, methylhydrogenpolysiloxane and a copolymer of dimethylsiloxane and methylphenylsiloxane, branched organopolysiloxane, cyclic siloxanes, such as octamethylcyclotetrasiloxane, decamethylcyclopentasiloxane, dodecamethylcyclohexasiloxane, tetramethyl-tetrahydrogencyclotetrasiloxane; silicone rubbers, such as gummy dimethylpolysiloxanes having high polymerization degrees and gummy dimethylsiloxane-methylphenylsiloxane copolymers having high polymerization degrees; and cyclosiloxane solutions of silicone rubber, trimethylsiloxysilicate, cyclosiloxane solutions of trimethylsiloxysilicate, higher alkoxy-modified silicones such as stearoxysilicone, higher fatty acid-modified silicones, alkyl-modified silicones, siliconols, fluorine-modified silicones, and solutions of silicone resins in a cyclic siloxane.

Preferably, at least apart of the unctuous agent (B) is a linear, branched or cyclic silicone oil represented by the formula, $R^6_f SiO_{(4-f)/2}$, wherein $R^6$ is a hydrogen, a $C_{1-30}$ alkyl, aryl, aralkyl, or fluorinated alkyl group and f is the number of from 0 to 2.5.

Examples of fluorine-containing oil include perfluoropolyether, perfluorodecalin, perfluorooctane, methylperfluorobutyl ether and ethylperfluoroisobutyl ether.

A content of these unctuous agents (B) in the cosmetic ranges preferably from 1 to 98 wt %, based on a total weight of the cosmetic.

The present cosmetic may contain (c) water according to intended use of the cosmetic. Rose water or lavender water can be used, too. An amount of water in the cosmetic ranges preferably from 1 to 95 wt %, based on a total weight of the cosmetic.

The cosmetic of the present invention may contain (D) a compound having an alcoholic hydroxyl group in addition to the aforementioned various components. Examples of the compound having an alcoholic hydroxyl group (D) include lower alcohols such as ethanol, propanol, and isopropanol; sugar alcohols such as sorbitol, maltose, and maltitol; sterols such as cholesterol, sitosterol, phytosterol, and lanosterol; polyalcohols such as butylene glycol, propylene glycol, dibutylene glycol, and pentylene glycol. An amount of the compound having an alcoholic hydroxyl group in the cosmetic ranges preferably from 0.1 to 98 wt %, based on a total weight of the cosmetic.

The present cosmetic may contain (E) a water-soluble or water-swellable polymer. Examples of the water-soluble or water-swellable polymer include gum Arabic, tragacanth gum, arabinogalactan, locust bean gum (carob gum), guar gum, karaya gum, carrageenan, pectin, agar-agar, quince seed (i.e., marmelo), starch from rice, corn, potato or wheat, algae colloid, and trant gum; bacteria-derived polymers such as xanthan gum, dextran, succinoglucan, and pullulan; animal-derived polymers such as collagen, casein, albumin, and gelatin; starch-derived polymers such as carboxymethyl starch and methylhydroxypropyl starch; cellulose polymers such as methyl cellulose, ethyl cellulose, methylhydroxypropyl cellulose, carboxymethyl cellulose, hydroxymethyl cellulose, hydroxypropyl cellulose, nitrocellulose, sodium cellulose sulfate, sodium carboxymethyl cellulose, crystalline cellulose, and cellulose powder; alginic acid-derived polymers such as sodium alginate and propylene glycol alginate; vinyl polymers such as polyvinyl methylether, polyvinylpyrrolidone, and carboxyvinyl polymer; polyoxyethylene polymers such as polyethylene glycol; polyoxyethylene/polyoxypropylene copolymers; acrylic polymers such as sodium polyacrylate, polyethyl acrylate, and polyacrylamide; polyethyleneimine; cationic polymers; and inorganic thickening agents such as, bentonite, aluminum magnesium silicate, montmorillonite, videlite, nontronite, saponite, hectorite, and silicic anhydride. Film forming polymers such as polyvinyl alcohol and polyvinylpyrrollidone are also included. An amount of the water-soluble or water-swellable polymer (E) in the cosmetic ranges preferably from 0.1 to 25 wt %, based on a total amount of the cosmetic.

The present cosmetic may contain (F) powder except the surface treated powder (A). Any powder which are commonly used in cosmetics may be used, regardless of the shape (spherical, rod-like, acicular, tubular, irregular, scaly or spindle forms), particle size (size of fume, fine particles or pigment grade), and particle structure (porous and non-porous), such as, for example, inorganic powder, organic powder, surface active, metal salt powder, colored pigments, pearl pigments, and metallic powder pigments.

Examples of the powder are as described above. Composite powder or powder treated with ester oil, fluorine oil, surfactant, or silicone except for the silicones of the present invention may be used. A mixture of two or more of powder may be used as required. A content of the powder in the cosmetic ranges preferably from 0.1 to 99 wt %, based on a total weight of the cosmetic. In a pressed powder cosmetics, the content ranges preferably from 80 to 99 wt %.

The present cosmetics may contain one or more of (G) a surfactant depending on intended use of cosmetics. Any surfactant commonly used in cosmetics may be used, for example, anionic, cationic, nonionic or amphoteric surfactant.

Examples of the anionic surfactant include fatty acid soaps, such as sodium stearate and triethanolamine palmitate, alkylether carboxylic acids and salts thereof, salts of condensates of amino acids with fatty acids, alkyl sulfonate salts, alkenesulfonates, sulfonates of fatty acid esters, fatty acid amide sulfonates, sulfonate salts of the formalin condensates, salts of alkyl sulfates, salts of secondary higher alcohol sulfates, salts of alkyl/allyl ether sulfates, salts of fatty acid ester sulfates, salts of fatty acid alkylolamide sulfates, and salts of Turkey Red oil sulfate, alkyl phosphate salts, ether phosphate salts, alkylallylether phosphate salts, amide phosphate salts, and N-acylamino surfactants.

Examples of the cationic surfactants include amine salts such as alkylamine salts, amine salts of polyamine and amino alcohol fatty acid derivatives, alkyl quaternary ammonium salts, aromatic quaternary ammonium salts, pyridinium salts and imidazolium salts.

Examples of the nonionic surfactants include sorbitan fatty acid esters, glycerin fatty acid esters, polyglycerin fatty acid esters, propylene glycol fatty acid esters, polyethylene glycol fatty acid esters, sucrose fatty acid esters, polyoxyethylene alkyl ethers, polyoxypropylene alkyl ethers, polyoxyethylene alkyl phenyl ether, polyoxyethylene fatty acid esters, polyoxyethylene sorbitan fatty acid esters, polyoxyethylene sorbitol fatty acid esters, polyoxyethylene glycerin fatty acid esters, polyoxyethylene propylene glycol fatty acid esters, polyoxyethylene castor oil, polyoxyethylene hydrogenated castor oil, polyoxyethylene phytostanol ether, polyoxyethylene phytosterol ether, polyoxyethylene cholestanol ether, polyoxyethylene cholesteryl ether, linear or branched-polyoxyalkylene-modified organopolysiloxane, linear or branched polyoxyalkylene/alkyl-comodified organopolysiloxane, linear or branched-polyglycerin-modified organopolysiloxane, linear or branched-polyglycerin/alkyl-comodified organopolysiloxane, alkanolamide, sugar ethers, and sugar amides.

Examples of the amphoteric surfactant include betaine, aminocarboxylates, imidazoline derivatives, and amide amine type.

A content of the surfactant in the cosmetic ranges preferably from 0.1 to 20 wt. %, particularly preferably from 0.2 to 10 wt. % relative to the total amount of the cosmetic.

The cosmetic according to the present invention may contain one or more of (H) crosslinked organopolysiloxane, depending on intended use of the cosmetic. Preferably, the crosslinked organopolysiloxane (H) is swelled with a silicone having a low viscosity from 0.65 mm$^2$/sec to 10.0 mm$^2$/sec, both viscosity measured at 25° C., in a larger amount than the organopolysiloxane itself. The crosslinked organopolysiloxane (H) has a crosslinkage having groups of the formula, —$C_xH_{2x}$—, at both terminals, wherein x is an integer of from 2 to 5, preferably 3. The crosslinkage can be derived from a diallyl compound. The crosslinkage preferably comprises at leas at one moiety selected from the group consisting of polyoxyalkylene residue, polyglycelin residue, alkyl group, alkylene group, aryl group, arylene group, fluoroalkyl group, and fluoroalkylene group. A content of the crosslinked organopolysiloxane (H) ranges preferably from 0.1 to 50 wt %, more preferably from 1 to 30 wt %, based on a total weight of the cosmetic.

The cosmetic according to the present invention may contain one or more of (I) silicone resin, except the silicone oil (B) and the aforesaid crosslinked organopolysiloxane. Preferably, the silicone resin(I) is an acrylic silicone resin such as an acrylic/silicone graft or an acrylic/silicone block copolymer. Other preferred silicone resin(I) includes silicone network compounds such as those represented as MQ, MDQ, MT, MDT, or MDTQ, wherein M is a trialkylsiloxy unit, D is a dialkylsiloxy unit, T is a triallkylsiloxy unit, and Q is tetra functional siloxy unit. The silicone resin(I) may comprises at least one anionic moiety selected from the group consisting of pyrrolidone residue, long-chain alkyl groups, polyoxyalkylene groups, fluoroalkyl groups, and carboxyl group. A content of the silicone resin(I) in the cosmetic ranges preferably from 0.1 to 20 wt %, more preferably from 1 to 10, based on a total weight of the cosmetic.

In the cosmetic of the present invention, other components that are commonly used in cosmetics can be incorporated in an amount not to adversely affect the cosmetic. Examples of the components include oil-soluble gelling agents, clay minerals modified with organic compounds, resins, antiperspirants, ultraviolet absorbents, ultraviolet absorbing and scattering agents, moisture retention agents, antiseptics, antimicrobial agents, perfumes, salts, antioxidants, pH regulators, a chelating agents, refreshing agents, an anti-inflammatory agent, skin beautifying components, such as skin whitener, cell activator, rough dry skin improver, blood circulation promoter, skin astringent and anti-seborrheic agent, vitamins, amino acids, nucleic acids, hormones, clathrate compounds, and hair setting agents.

Examples of the oil-soluble gelling agent include metal soaps, such as aluminum stearate, magnesium stearate and zinc myristate; amino acid derivatives, such as N-lauroyl-L-glutamic acid and $\alpha,\gamma$-di-n-butylamine; dextrin fatty acid esters, such as dextrin palmitic acid ester, dextrin stearic acid ester and dextrin 2-ethylhexaminic acid palmitic acid ester; inulin fatty acid esters such as fructooligostearate; sucrose fatty acid esters, such as sucrose palmitic acid ester and sucrose stearic acid ester; benzylidene derivatives of sorbitol, such as monobenzylidene sorbitol and dibenzylidene sorbitol; and clay minerals modified with organic compounds, such as dimethylbenzyldodecyl ammonium montmorillonite clay and dimethyldioctadecyl ammonium montmorillonite clay.

Examples of the antiperspirant include aluminum chlorohydrate, aluminum chloride, aluminum sesquichlorohydrate, zirconium hydoxychloride, aluminum zirconium hydroxychloride, and aluminum zirconium glycine complex.

Examples of the ultraviolet absorbents include ultraviolet absorbents of benzoic acid type, such as p-aminobenzoic acid; those of anthranilic acid type, such as methyl anthranilate; those of salicylic acid type, such as methyl salicylate; those of succinic acid type, such as octyl p-methoxysuccinate; those of benzophenone type, such as 2,4-dihydroxybenzophenone; those of urocanic acid type, such as ethyl urocanate; and those of dibenzoylmethane type, such as 4-t-butyl-4'-methoxydibenzoylmethane. Examples of the ultraviolet absorbing and scattering agents include fine powder of titanium oxide, fine powder of iron-containing titanium oxide, fine powder of zinc oxide, fine powder of cerium oxide, and a mixture thereof.

Examples of moisture retention agents include glycerin, sorbitol, propylene glycol, dipropylene glycol, 1,3-butylene glycol, pentylene glycol, glucose, xylitol, maltitol, polyethylene glycol, hyaluronic acid, chondroitin sulfuric acid, pyrrolidone carboxylate, polyoxyethylene glycoside, and polyoxypropylene methylglycoside.

Examples of the antiseptics include alkyl paraoxybenzoates, benzoic acid, sodium benzoate, sorbic acid, potassium sorbate, and phenoxyethanol may be used. For the antibacterial agents, benzoic acid, salicylic acid, carbolic acid, sorbic acid, paraoxybenzoic acid alkyl esters, parachlorometha-cresol, hexachlorophene, benzalkonium chloride, chlorohexydine chloride, trichlorocarbanilide and phenoxyethanol.

Examples of the salts include inorganic salts, organic acid salts, salts of amine and salts of amino acids. Examples of the inorganic salts include sodium, potassium, magnesium, calcium, aluminum, zirconium, or zinc salt of inorganic acid such as hydrochloric acid, sulfuric acid, carbonate acid, and nitric acid. Examples of the salts of organic acid include salts of organic acid such as acetic acid, dehydroacetic acid, citric acid, malic acid, succinic acid, ascorbic acid, and stearic acid. Examples of the salts of amine or amino acid include salt of triethanol amine and salt of glutamic acid. Other examples are salt of hyaluronic acid, chondroitin sulfate, aluminum/zirconium/glycine chelate, and salts produced by acid-alkaline neutralization reaction in the cosmetic.

Examples of the antioxidants include tocopherol, butylhydroxyanisole, dibutylhydroxytoluene and phytic acid; examples of the pH regulators include lactic acid, citric acid, glycolic acid, succinic acid, tartaric acid, dl-malic acid, potassium carbonate, sodium hydrogen carbonate and ammonium hydrogen carbonate; examples of the chelating agents include alanine, sodium ethylenediamine tetraacetate, sodium polyphosphate, sodium metaphosphate and phosphoric acid; examples of the refrigerants include L-menthol and camphor; and examples of the anti-inflammatory agents include allantoin, glycyrrhizin and salts thereof, glycyrrhetinic acid and stearyl glycyrrhetinate, tranexamic acid and azulene.

Examples of the skin-beautifying components include whitening agents, such as placenta extract, arbutin, glutathione and Yukinoshita extract; cell activators, such as royal jelly, photosensitizers, cholesterol derivatives and calf blood extract; rough and dry skin improvers; blood circulation improvers, such as nonylic acid vanillyl amide, benzyl nicotinate, beta-butoxyethyl nicotinate, capsaicin, zingerone, cantharis tincture, ichtammol, caffeine, tannic acid, alphaborneol, tocopheryl nicotinate, inositol hexanicotinate, cyclandelate, cinnarizine, tolazoline, acetyl choline, verapamil, cepharanthin and gamma-oryzanol; skin astringents, such as zinc oxide and tannic acid; and anti-seborrheic agents, such as sulfur and thianthol.

Examples of the vitamins include vitamin A, such as vitamin A oil, retinol, retinyl acetate and retinyl palmitate; vitamin B, including vitamin $B_2$ such as riboflavin, riboflavin butyrate and flavin adenine nucleotide, vitamin $B_6$ such as pyridoxine hydrochloride, pyridoxine dioctanoate and pyridoxine tripalmitate, vitamin $B_{12}$ and its derivatives, and vitamin B15 and its derivatives; vitamin C, such as L-ascorbic acid, L-ascorbic acid dipalmitic ester, sodium (L-ascorbic acid)-2-sulfate and dipotassium L-ascorbic acid diphosphate; vitamin D, such as ergocalciferol and cholecarciferol; vitamin E, such as alpha-tocopherol, beta-tocopherol, gamma-tocopherol, dl-alpha-tocopheryl acetate, dl-alpha-tocopheryl nicotinate and dl-alpha-tocopheryl succinate; vitamin H; vitamin P; nicotinic acids, such as nicotinic acid, benzyl nicotinate and nicotinic acid amide; pantothenic acids, such as calcium pantothenate, D-pantothenyl alcohol, pantothenyl ethyl ether and acetylpantothenyl ethyl ether; and biotin.

Examples of the amino acids include glycine, valine, leucine, isoleucine, serine, threonine, phenylaranine, alginine, lysine, aspartic acid, glutamic acid, cystine, cysteine, methionine, and tryptophan; examples of the nucleic acids include deoxyribonucleic acid; and examples of the hormones include estradiol and ethenyl estradiol.

Examples of the polymers for hair setting include amphoteric, anionic, cationic, and nonionic polymers, such as polymers of polyvinyl pyrrolidone type such as polyvinyl pyrrolidone, vinyl pyrrolidone/vinyl acetate copolymers; acidic polymers of vinyl acetate ether type such as methyl vinyl ether/maleic acid anhydride alkyl half ester copolymer; polymers of acidic polyvinyl acetate type such as vinyl acetate/crotonic acid copolymer; acidic acrylic polymers such as (meth)acrylic acid/alkyl (meth) acrylate copolymer, (meth) acrylic acid/alkyl (meth) acrylate/alkyl acrylic amide copolymer, and amphoteric acrylic polymer such as N-methacryloylethyl-N,N-dimethylammonium alpha-N-methylcarboxybetaine/alkylmetahcrylate copolymer, hydroxypropyl (meth)acrylate/butylaminoethyl methacrylate/octyl amide of acrylic acid copolymer. Use is also made of naturally occurring polymers such as cellulose or derivatives thereof, keratin, collagen and derivatives thereof.

The term "cosmetic materials" as used herein are intended to include skin care products, such as face lotion, milky lotion, cream, face cleansing cream, massage materials, toilet soap and detergent, antiperspirant and deodorant; makeup products, such as face powder, foundation, rouge, eye shadow, mascara, eyeliner and lipstick; and hairdressing products, such as shampoo, rinse, treatment setting agent, antiperspirant and ultraviolet protection cosmetics, such as sunscreen milky lotion or sunscreen cream.

Further, the present cosmetic materials may be in various forms such as liquid, emulsion, solid, paste, gel, powder, press, laminate, mousse, spray, stick, pencil forms.

EXAMPLES

The present invention will be further explained in detail below by referring to Examples, but not limited thereto. In the following, "%" means "% by weight" unless otherwise specified.

Preparation Example 1

Preparation of Organopolysiloxane (I)

In a glass flask equipped with a stirrer, thermometer, and reflux condenser, 270 g of methyltriethoxysilane, 90 g of ethanol and 1.5 g of ion exchange resin, Purolite CT-169DR, ex Purolite International Ltd., were placed and mixed, to which 24 g of water was added. The mixture was subjected to reaction for one hour at room temperature and two hours under the reflux of ethanol. Then, ethanol was distilled off at atmospheric pressure to obtain condensate of hydrolyzed methyltriethoxysilane having a viscosity of 21 mm$^2$/g at 25° C. and a number average molecular weight, reduced to polystyrene, of 1000.

Preparation Example 2

Preparation of Organopolysiloxane (II)

In a glass flask equipped with a stirrer, thermometer, and reflux condenser, 600 parts by weight of the organohydrogensiloxane of the following formula (10),

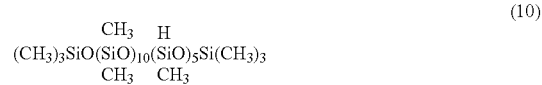

(10)

800 parts by weight of toluene, and 2 parts by weight of 0.5 wt % solution of chloroplatinic acid in toluene, to which 1490 parts by weight of the organopolysiloxane of the following formula (11) was added dropwise,

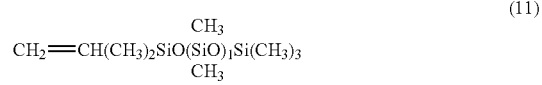

(11)

followed by adding dropwise 110 parts by weight of vinyltriethoxysilane. The mixture was subjected to reaction for 6 hours under reflux. The reaction mixture was heated under vacuum to remove the solvent and the organopolysiloxane of the following compositional formula (12) was obtained.

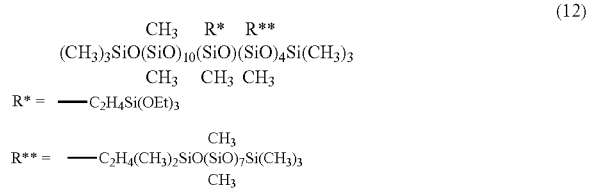

(12)

$$(CH_3)_3SiO(SiO)_{10}(SiO)(SiO)_4Si(CH_3)_3$$
with $CH_3$, $CH_3$, $CH_3$ groups $R^* = $ —$C_2H_4Si(OEt)_3$ $R^{**} = $ —$C_2H_4(CH_3)_2SiO(SiO)_7Si(CH_3)_3$ with $CH_3$ The organopolysiloxane was transparent colorless liquid having a viscosity of 57 mm²/g at 25° C. and a specific gravity of 0.958 at 25° C.

Preparation Example 3

Preparation of Acrylic/Silicone Graft Copolymer (III)

In a glass flask equipped with a stirrer, thermometer, and reflux condenser, 100 parts by weight of the organohydrogensiloxane of the following formula (13),

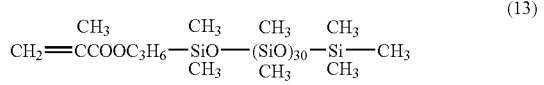

(13)

$$CH_2=CCOOC_3H_6-SiO-(SiO)_{30}-Si-CH_3$$

10 parts by weight of methyl methacrylate, 80 parts by weight of stearyl methacrylate, 10 parts by weight of γ-methacryloxypropyl trimethoxysilane, 200 parts by weight toluene and 4 parts by weight of azobisisobutyronitrile were placed and subjected to polymerization at a temperature of 100° C. under nitrogen flow for 10 hours. Subsequently, toluene was distilled off under vacuum to obtain acrylic/silicone graft copolymer. The copolymer was solid having light yellow color and a melting point of 30° C. By GPC analysis, the polymer was found to have a weight average molecular weight, reduced to polystyrene, of 42,000.

Examples 1-9, Comparative Examples 1-6, Reference Examples 1-2

In a reactor, 98 parts by weight of titanium oxide, ex Ishihara Sangyo Kaisha, LTD., or 95 parts by weight of sericite, ex Sanshin Kokogyo Corp., both of which had been pretreated by vacuum drying while heating, were placed to which ca. 30 wt % solution of each of the organopolysiloxanes prepared in the Preparation Examples of 1-3 and commercially available treatment agent 1, i.e., methylhydrogenpolysiloxane sold under the trade name of KF-99P, ex Shin-Etsu Chemical Co., Ltd, in toluene in an amount as shown in Table 1 in parts by weight was gradually added while stirring. Subsequently, toluene was distilled off at an elevated temperature and then the mixture of the powder and the organopolysiloxanes was subjected to a reaction at 150° C. for 3 hours.

TABLE 1

| Surface Treated powder | Powder | | Treatment combination | | | |
|---|---|---|---|---|---|---|
| | Titanium oxide | Sericite | Prep. Ex.*³1 | Prep. Ex. 1 | Prep. Ex. 2 | Treatment agent 1 |
| Example 1 | 98 | | 1 | 1 | | |
| Example 2 | 98 | | 1 | | | 1 |
| Example 3 | 98 | | 0.6 | 1.4 | | |
| Example 4 | 98 | | 1.4 | 0.6 | | |
| Example 5 | | 97 | 1.5 | 1.5 | | |
| Example 6 | | 97 | 1.5 | | 1.5 | |
| Example 7 | | 97 | 1.2 | 0.9 | 0.9 | |
| Example 8 | | 97 | 0.9 | 2.1 | | |
| Example 9 | | 97 | 2.1 | 0.9 | | |
| Comp. Ex. *¹1 | 98 | | 2 | | | |
| Comp. Ex. 2 | 98 | | | 2 | | |
| Comp. Ex. 3 | 98 | | | | | 2 |
| Comp. Ex. 4 | | 97 | 3 | | | |
| Comp. Ex. 5 | | 97 | | | 3 | |
| Comp. Ex. 6 | | 97 | | | | 3 |
| Ref. Ex. *²1 | Blend of titanium oxide of Comp. Ex. 1 and Comp. Ex. 2 in 1:1 weight | | | | | |
| Ref. Ex. 2 | Blend of Sericite of Comp. Ex. 4 and Comp. Ex. 5 in 1:1 weight | | | | | |

*¹Comp. Ex.: Comparative Example.
*²Ref. Ex.: Reference Example.
*³Prep. Ex.: Preparation Example On each of the surface treated powder thus obtained, surface activity, water resistance, and amount of evolved hydrogen gas were measured. Results are as shown in Table 2.

TABLE 2

| Surface treated powder | Surface activity (ΔE) | Water resistance (hr) | Evolved hydrogen gas(cc/g) |
|---|---|---|---|
| Example 1 | 1.5 | 5.0 | 0 |
| Example 2 | 1.9 | 4.5 | 0 |
| Example 3 | 1.2 | 5.5 | 0 |
| Example 4 | 1.5 | 5.0 | 0 |
| Example 5 | 0.5 | 5.5 | 0 |
| Example 6 | 0.4 | 5.0 | 0 |
| Example 7 | 0.4 | 5.0 | 0 |
| Example 8 | 0.5 | 5.0 | 0 |
| Example 9 | 0.5 | 4.5 | 0 |
| Comp. Ex. 1 | 2.5 | 0.4 | 0 |
| Comp. Ex. 2 | 2.7 | 1.0 | 0 |
| Comp. Ex. 3 | 2.9 | 3.5 | 2.5 |
| Comp. Ex. 4 | 0.9 | 0.3 | 0 |
| Comp. Ex. 5 | 0.8 | 0.8 | 0 |
| Comp. Ex. 6 | 0.8 | 3.5 | 4.6 |
| Ref. Ex. 1 | 2.5 | 0.5 | 0 |
| Ref. Ex. 2 | 0.8 | 0.5 | 0 |

Methods of the measurements are as follows.

(1) Surface Activity

Forty parts by weight of the powder were mixed with 60 parts by weight of castor oil. A predetermined amount of the mixture was sandwiched between glass plates through which UV-ray was radiated. Color of the powder before and after the radiation was measured by a colorimeter and a difference in color, ΔE, was determined. Higher surface activity shows greater ΔE.

(2) Water Resistance

A predetermined amount of the surface treated powder was pressed in an aluminum dish having a diameter of 50 mm. At the center of a surface of the powder disk thus obtained, a mixed solution of 1,3-butyleneglycol and water in a ratio of 1:1 was dropped and a time for the drop to penetrate in the disk was measured. Longer time means higher water resistance of the powder composed of the disk.

(3) Amount of Hydrogen Gas Evolved

A predetermined amount of the surface treated powder was dispersed in toluene, to which 20% KOH alkaline solution was dropped. A volume of hydrogen gas evolved from the powder due to remaining Si—H groups was measured.

As can be seen from Table 2, the powder of the present Examples did not evolve hydrogen, and were superior in the surface activity and water resistance compared with the Comparative Examples. The powder of the Comparative Examples 3 and 6 were highly resistant to water. However, they evolved much hydrogen, indicating that many unreacted Si—H groups remained.

The Comparative Examples 1, 2, 4 and 5, are the powder treated with one kind of organopolysiloxane. They did not evolve hydrogen, but disks thereof absorbed the drop of the mixture of water and 1,3-butyleneglycol quickly, indicating lower water resistance.

The Reference Examples 1 and 2 had higher surface activity and lower water resistance compared with Examples 1 and 4, respectively. Particularly, the values of water resistance were close to those of worse Comparative Example, that it, water resistance value of the Reference Example 1 was close to that of the Comparative Example 1, and water resistance value of the Reference Example 2 was close to that of Comparative Example 4, respectively.

From the above results, the present surface treatment combination attains synergistic effects of the components.

Examples 10-11, Comparative Examples 7-8, Reference Example 3

Using the surface treated powder prepared in Examples 1, 2, 5, 6, Comparative Examples 1 to 4, and Reference Examples 1 and 2, foundations were prepared according to the formulations shown in the following table and evaluated.

Preparation Procedures

A: Components 1-14 were mixed and pulverized

B: To the powder mixture from A, components 15-17 were added and pulverized further.

C: The powder mixture from B was pressed into a powder foundation.

The obtained foundations were rated on comfortableness to use, spreadability, uniformity of color, and durability by 50 women panelists according to the following criteria.

|  | comfortableness to use, durability | spreadability | uniformity of color |
|---|---|---|---|
| 5 points | Excellent | Excellent | Excellent |
| 4 points | Good | Good | Good |
| 3 points | Average | Average | Average |
| 2 points | Slightly bad | Slightly heavy | Slightly bad |
| 1 point | Bad | Heavy | Bad |

The ratings were averaged and evaluation results according to the following criteria were obtained as shown in the Table 3.

| Evaluation criteria | |
|---|---|
| Averaged points | |
| 4.5 or higher | A |
| 3.5 or higher to lower than 4.5 | B |
| 2.5 or higher to lower than 3.5 | C |
| 1.5 or higher to lower than 2.5 | D |
| Lower than 1.5 | E |

| | | Content, parts by weight | | | |
|---|---|---|---|---|---|
| | Component | Example 10 | Example 11 | Comp. Ex. 7 | Comp. Ex. 8 | Ref. Ex. 3 |
| 1 | Titanium oxide (Example 1) | 12 | — | — | — | — |
| 2 | Sericite (Example 5) | 35 | — | — | — | — |
| 3 | Titanium oxide (Example 2) | — | 12 | — | — | — |
| 4 | Sericite (Example 6) | — | 35 | — | — | — |
| 5 | Titanium oxide (Comp. Ex. 1) | — | — | 12 | — | — |
| 6 | Sericite (Comp. Ex. 4) | — | — | 35 | — | — |
| 7 | Titanium oxide (Comp. Ex. 3) | — | — | — | 12 | — |
| 8 | Sericite (Comp. Ex. 6) | — | — | — | 35 | — |
| 9 | Titanium oxide (Ref. Ex. 1) | — | — | — | — | 12 |
| 10 | Sericite ((Ref. Ex. 2) | — | — | — | — | 15 |
| 11 | Talc treated with Lecithin | 35.1 | 35.1 | 35.1 | 35.1 | 35.1 |
| 12 | Nylon powder treated with Lecithin | 5 | 5 | 5 | 5 | 5 |
| 13 | Iron oxide red | 0.4 | 0.4 | 0.4 | 0.4 | 0.4 |
| 14 | Iron oxide yellow | 2 | 2 | 2 | 2 | 2 |
| 15 | Amber | 0.4 | 0.4 | 0.4 | 0.4 | 0.4 |
| 16 | Iron oxide black | 0.1 | 0.1 | 0.1 | 0.1 | 0.1 |
| 17 | Dimethylpolysiloxane (6 mm$^2$/sec at 25° C.) | 7 | 7 | 7 | 7 | 7 |
| 18 | Glyceryl trioctanoate | 1.5 | 1.5 | 1.5 | 1.5 | 1.5 |
| 19 | Dipentaerythritol fatty acid ester | 1.5 | 1.5 | 1.5 | 1.5 | 1.5 |

TABLE 3

|  | Example 10 | Example 11 | Comparative Example 7 | Comparative Example 8 | Reference Example 3 |
|---|---|---|---|---|---|
| Comfortableness to use | A | A | C | D | C |
| Spreadability | A | A | B | C | C |
| Uniformity of color | B | B | C | B | B |
| Durability | A | A | C | C | C |

As shown in Table 3, the foundations of Examples 10 and 11 spread more lightly on the skin than those of the Comparative and Reference Examples; and applied foundations were more durable compared with those of the Comparative and Reference Examples.

After the completion of the aforesaid step B in the preparation procedures of the foundation, a predetermined amount of each mixture was taken into a container and the container was sealed. After keeping the mixture for 30 days, it was observed that the container containing the powder of the Comparative Example 7 treated with methylhydrogenpolysiloxane (KF-99P) bulged due to hydrogen gas originating from unreacted Si—H bonds.

The followings are formulation examples of the cosmetics of the present invention. The powder were prepared in the same manner as described above in Examples 1-9. Stability with time was evaluated by keeping a cosmetic at 50° C. for about 60 days and visually observing the cosmetic for any change in appearance.

Example 12

Oil-in-Water Type Cream

| Component | Wt % |
|---|---|
| 1. Ethanol | 17.0 |
| 2. Propylene glycol | 3.0 |
| 3. Polyether-modified silicone[1] | 0.5 |
| 4. Glyceryl trioctanoate | 2.0 |
| 5. Sericite treated with organopolysiloxane from Preparation Example 3 | 3.0 |
| 6. Composite powder of hybrid silicone[2] | 5.0 |
| 7. Carboxyvinyl polymer (1% aqueous solution) | 20.0 |
| 8. Xanthan gum (2% aqueous solution) | 6.0 |
| 9. Triethanolamine | 0.2 |
| 10. Antiseptics agent | q.s. |
| 11. Perfume | q.s. |
| 12. Purified water | 43.3 |

[1] Polyether-modified silicone; KF-6011, from Shin-Etsu Chemical Co., Ltd.
[2] Composite powder of hybrid silicone; KSP-100, from Shin-Etsu Chemical Co., Ltd.

Preparation Procedures

A: Components 1 to 6 were mixed.

B: Components 7 to 12 were mixed.

C: The mixture obtained in A was added to the mixture obtained in B and emulsified by stirring.

The oil-in-water type cream thus obtained had a fine texture, spread lightly on the skin and gave refreshing feel to the skin with no tackiness.

Example 13

Body Lotion

| Component | Wt % |
|---|---|
| 1. Etahnol | 17.0 |
| 2. 1,3-butylene glycol | 3.0 |
| 3. Branched polyglycerin-modified silicone[1] | 0.5 |
| 4. Glyceryl trioctanoate | 2.0 |
| 5. Talc treated with organopolysiloxane[2] | 5.0 |
| 6. Composite powder of hybrid silicone[3] | 5.0 |
| 7. Ammonium acryloyldimethyltaurine/VP copolymer (2% aqueous solution) | 20.0 |
| 8. xanthan gum (2% aqueous solution) | 6.0 |
| 9. Sodiume chloride (1% aqueous solution) | 1.0 |
| 10. Antiseptics agent | q.s. |
| 11. Perfume | q.s |
| 12. Pruified water | 40.5 |

[1] Branched polyglycerin-modified silicone; KF-6100 from Shin-Etsu Chemical Co., Ltd.
[2] In the method as described above, 98 parts by weight of powder was treated with 2 parts by weight of 1/1 mixture of the organopolysiloxane of the Preparation Example 1 and the organopolysiloxane of the Preparation Example 2.
[3] Composite powder of hybrid silicone; KSP-100 from Shin-Etsu Chemical Co., Ltd.

Preparation Procedures

A: Components 1 to 6 were mixed.

B: Components 7 to 12 were mixed.

C: The mixture obtained in A was added to the mixture obtained in B.

The body lotion obtained had a fine texture and was stable with time. It spread lightly on the skin to give refreshing feel with no oiliness.

Example 14

Oil-in-Water Type Cream

| Component | Wt % |
|---|---|
| 1. Crosslinked dimethylpolysiloxane[1] | 10.0 |
| 2. Glyceryl trioctanoate | 5.0 |
| 3. Dipropylene glycol | 7.0 |
| 4. Glycerin | 5.0 |
| 5. Methyl cellulose (2% aqueous solution)[2] | 7.0 |
| 6. Emulsifier of polyacrylic amide type[3] | 2.0 |
| 7. Mica titanium treated with organopolysiloxane[4] | 1.0 |
| 8. Antiseptics | q.s. |

-continued

| Component | Wt % |
|---|---|
| 9. Perfume | q.s. |
| 10. Purified water | 63.0 |

[1] Crosslinked dimethylpolysiloxane; KSG-16 from Shin-Etsu Chemical Co., Ltd.
[2] Methyl cellulose; Metholose SM-4000 from Shin-Etsu Chemical Co., Ltd.
[3] Emulsifier of polyacrylic amide type; Sepigel 305 from SEPIC
[4] Mica titanium was treated with a 1/1 in weight mixture of the organopolysiloxane prepared in the Preparation Example 1 and the organopolysiloxane prepared in the Preparation Example 2 in the same manner as described above.

Preparation Procedures

A: Components 3 to 10 were mixed.
B: Components 1 and 2 were mixed.
C: The mixture obtained in A was added to the mixture obtained in B and emulsified by stirring.

The oil-in-water type cream thus obtained had a fine texture and good stability, spread lightly on the skin and gave refreshing feel to the skin with no tackiness.

Example 15

Oil-in-Water Type Cream

| Component | Wt % |
|---|---|
| 1. Crosslinked dimethylpolysiloxane[1] | 8.0 |
| 2. Crosslinked dimethylpolysiloxane[2] | 30.0 |
| 3. Decamethylcyclopentasiloxane | 10.0 |
| 4. 1,3-butyleneglycol | 3.0 |
| 5. Branched polyglycerin-modified silicone[3] | 0.6 |
| 6. Branched polyglycerin-modified silicone[4] | 0.3 |
| 7. Emulsifier of polyacrylic amide type[5] | 2.0 |
| 8. Mica titanium treated with organopolysiloxane[6] | 1.0 |
| 9. Ammonium acryloyldimethyltaurine/VP copolymer (5% aqueous solution) | 13.0 |
| 10. Sodium chloride (1% solution) | 8.0 |
| 11. Antiseptics | q.s. |
| 12. Perfume | q.s. |
| 13. Purified water | 25.5 |

[1] Crosslinked dimethylpolysiloxane; KSG-15 from Shin-Etsu Chemical Co., Ltd.
[2] Crosslinked dimethylpolysiloxane; KSG-16 from Shin-Etsu Chemical Co., Ltd.
[3] Branched polyglycerin-modified silicone; KF6100 from Shin-Etsu Chemical Co., Ltd.
[4] Branched polyglycerin-modified silicone; KF6104 from Shin-Etsu Chemical Co., Ltd.
[5] Emulsifier of polyacrylic amide type; Simulgel 500 from SEPIC
[6] Mica titanium treated in the same manner as described above.

Preparation Procedures

A: Components 4 to 13 were mixed.
B: Components 1 to 3 were mixed.
C: The mixture obtained in A was added to the mixture obtained in B and emulsified by stirring.

The oil-in-water type cream thus obtained had a fine texture with very small droplets of oil in the internal phase. The cream was stable with time, spread lightly on the skin and gave refreshing feel to the skin with no tackiness.

Example 16

Water-in-Oil Type Cream

| Component | Wt % |
|---|---|
| 1. Dimethylpolysiloxane (6 mm$^2$/sec at 25° C.) | 6.0 |
| 2. Methylphenylpolysiloxane | 4.0 |
| 3. Squalane | 5.0 |
| 4. Neopentylglycol dioctanoate | 3.0 |
| 5. Polyether-modified silicone[1] | 3.0 |
| 6. Fine particulate of hydrophobized titanium dioxide[2] | 2.0 |
| 7. Magnesium sulfate | 0.7 |
| 8. Glycerin | 10.0 |
| 9. Antiseptics | q.s. |
| 10. Perfume | q.s. |
| 11. Purified water | balance |

[1] Polyether-modified silicone; KF 6012 from Shin-Etsu Chemical Co., Ltd..
[2] Fine particulate of hydrophobized titanium powder; fine particulate of titanium oxide with average particle diameter of 0.05 μm was dispersed in water so that the content of titanium would be 10 wt. %. Then 10 wt. % sodium silicate solution, where the molar ratio of $SiO_2/Na_2O = 0.5$, was added in such an amount that a $SiO_2$ content corresponds to 2 wt. % relative to titanium dioxide. Subsequently, 10 wt. % aluminum sulfate solution was added dropwise in such an amount that the $Al_2O_3$ content corresponds to 7.5 wt. % relative to titanium dioxide to deposit silicic acid hydrate and alumina hydrate on the surface of titanium dioxide. After the reaction was completed, the reactant was filtered, washed, dried and pulverized with the aid of a jet mill. The resulting particulate in an amount of 98 parts by weight was placed in Henschel mixer, to which 2 parts by weight of with the 1/1 in weight mixture of the organopolysiloxane prepared in the Preparation Example 1 and the organopolysiloxane prepared in the Preparation Example 2 was added while stirring sufficiently, and then subjected to reaction at 120° C.

Preparation Procedures

A: Components 1 to 5 were mixed and then component 6 was added.
B: Components 7 to 9 and 11 were mixed.
C: While stirring, the mixture obtained in B was added dropwise to the mixture obtained in A. The resulting mixture was emulsified, to which component 10 was added.

The water-in-oil cream thus obtained had a fine texture and good stability, spread lightly on the skin and gave refreshing feel to the skin with no stickiness.

Example 17

Water-in-Oil Cream

| Component | Wt % |
|---|---|
| 1. Crosslinked polyether-modified silicone[1] | 4.0 |
| 2. Crosslinked dimethylpolysiloxane[2] | 3.0 |
| 3. Branched polyether-modified silicone[3] | 1.0 |
| 4. Dimethylpolysiloxane (6 mm$^2$/sec at 25° C.) | 10.0 |
| 5. Sericite treated with organopolysiloxane from Preparation Example 3 | 2.0 |
| 6. 1,3-Butylene glycol | 8.0 |
| 7. Ethanol | 5.0 |
| 8. Sodium citrate | 0.2 |
| 9. Sodium chloride | 0.5 |
| 10. Antiseptics | q.s. |
| 11. Perfume | q.s. |
| 12. Purified water | 66.3 |

[1] Crosslinked polyether-modified silicone, KSG-210 from Shin-Etsu Chemical Co., Ltd..
[2] Crosslinked dimethylpolysiloxane, KSG-15 from Shin-Etsu Chemical Co., Ltd..
[3] Branched polyether-modified silicone, KF-6028 from Shin-Etsu Chemical Co., Ltd..

Preparation Procedures
A: Components 3 to 5 were mixed and then components 1 and 2 were added.
B: Components 6 to 10 and 12 were mixed.
C: The mixture obtained in B was added to the mixture obtained in A and emulsified by stirring, to which component 11 was added and emulsified.

The water-in-oil cream thus obtained had a fine texture and good stability, spread lightly on the skin and gave refreshing feel to the skin with no stickiness.

Example 18

Water-in-Oil Makeup Base

| Component | Wt % |
| --- | --- |
| 1. Crosslinked polyether-modified silicone[1] | 4.0 |
| 2. Crosslinked dimethylpolysiloxane[2] | 2.0 |
| 3. Branched polyether-modified silicone[3] | 0.5 |
| 4. Dimethylpolysiloxane (6 mm$^2$/sec at 25° C.) | 7.0 |
| 5. Dimethylpolysiloxane (20 mm$^2$/sec at 25° C.) | 2.0 |
| 6. Talc treated with organopolysiloxane[4] | 2.0 |
| 7. Titanium oxide fine powder dispersion[5] | 10.0 |
| 8. 1,3-Butylene glycol | 8.0 |
| 9. Ethanol | 5.0 |
| 10. Methylcellulose (2% aqueous solution)[6] | 2.5 |
| 11. Sodium citrate | 0.2 |
| 12. Sodium chloride | 0.5 |
| 13. Antiseptics | q.s. |
| 14. Perfume | q.s. |
| 15. Purified water | 61.3 |

[1]Crosslinked polyether-modified silicone, KSG-210 from Shin-Etsu Chemical Co., Ltd..
[2]Crosslinked dimethylpolysiloxane, KSG-15 from Shin-Etsu Chemical Co., Ltd..
[3]Branched polyether-modified silicone KF-6028 from Shin-Etsu Chemical Co., Ltd..
[4]Titanium oxide in an amount of 98 parts by weight was treated with 1 parts by weight of a 1/1 mixture of the organosiloxane prepared in the Preparation Example 1 and the organosiloxane prepared in the Preparation Example 2 in the same manner as described above.
[5]Titanium oxide fine powder dispersion, SPD-T5 from Shin-Etsu Chemical Co., Ltd..
[6]Methyl cellulose, Metholose 65-SH4000 from Shin-Etsu Chemical Co., Ltd..

Preparation Procedures
A: Components 1 to 7 were mixed.
B: Components 8 to 13 and 15 were mixed.
C: The mixture obtained in B was added to the mixture obtained in A and emulsified by stirring, to which component 14 was added.

The water-in-oil makeup base thus obtained had a fine texture and good stability, spread lightly on the skin and gave refreshing feel to the skin with no stickiness. The applied base was durable and resistant to sweat.

Example 19

Water-in-Oil Type Cream

| Component | Wt % |
| --- | --- |
| 1. Alkyl-modified crosslinked polyether-modified silicone[1] | 4.0 |
| 2. Alkyl-modified crosslinked polyether-modified silicone[2] | 6.0 |
| 3. Alkyl/polyether co-modified silicone[3] | 0.5 |
| 4. Liquid paraffin | 12.0 |
| 5. Neopentylglycol dioctanoate | 5.0 |
| 6. Composite powder of hybrid silicone[4] | 1.5 |
| 7. Titanium oxide fined powder treated with the organopolysiloxane of Example 2 | 2.0 |
| 8. Glycerin | 3.0 |

-continued

| Component | Wt % |
| --- | --- |
| 9. 1,3-butylene glycol | 7.0 |
| 10. Sodium citrate | 0.2 |
| 11. Sodium chloride | 0.5 |
| 12. Antiseptics | q.s. |
| 13. Perfume | q.s. |
| 14. Purified water | 58.3 |

[1]Alkyl-modified crosslinked polyether-modified silicone; KSG-310 from Shin-Etsu Chemical Co., Ltd.
[2]Alkyl-modified crosslinked polyether-modified silicon; KSG-41 from Shin-Etsu Chemical Co., Ltd.
[3]Alkyl/polyether co-modified silicone; KF-6038 from Shin-Etsu Chemical Co., Ltd.
[4]Composite powder of hybrid silicone; KSP-100 from Shin-Etsu Chemical Co., Ltd.

Preparation Procedures
A: Components 1 to 7 were mixed.
B: Components 8 to 12 and 14 were mixed.
C: The mixture obtained in B was added to the mixture obtained in A and emulsified by stirring, to which component 13 was added.

The water-in-oil cream thus obtained had a fine texture and good stability, spread lightly on the skin and gave refreshing feel to the skin with no stickiness.

Example 20

Eyeliner

| Component | Wt % |
| --- | --- |
| 1. Decamethylpentasiloxane | 39.0 |
| 2. Branched polyether-modified silicone[1] | 3.0 |
| 3. Organosilicone resin[2] | 15.0 |
| 4. Organo-modified Betnite | 3.0 |
| 5. Iron oxide black treated with organopolysiloxane[3] | 10.0 |
| 6. 1.3-Butylene glycol | 5.0 |
| 7. Sodium dehydroacetate | q.s. |
| 8. Antiseptics | q.s. |
| 9. Purified water | 25.0 |

[1]Polyether-modified silicone; KF6028 from Shin-Etsu Chemical Co., Ltd.
[2]Organosilicone resin; KF-7312J from Shin-Etsu Chemical Co., Ltd.
[3]Iron oxide black in an amount of 98 parts by weight was treated with 2 parts by weight of the 1/1 mixture of the organopolysiloxane of the Preparation Example 1 and the organopolysiloxane of the Preparation Example 2 in the same manner as described above.

Preparation Procedures
A: Components 1 to 4 were mixed, to which component 5 was added and mixed.
B: Components 6 to 9 were mixed.
C: The mixture obtained in B was added to the mixture obtained in A and emulsified by stirring.

The eyeliner thus obtained had a fine texture and good stability. It was smooth to draw and gave refreshing feel to the skin with no stickiness. The applied eyeliner was resistant to water and sweat, and durable.

Example 21

Eyeliner

| Component | Wt % |
| --- | --- |
| 1. Decamethylcyclopentasiloxane | 6.0 |
| 2. Dimethylpolysiloxane (6 mm$^2$/sec at 25° C.) | 5.0 |

-continued

| Component | Wt % |
|---|---|
| 3. Jojoba oil | 2.0 |
| 4. Polyether-modified silicone[1] | 1.0 |
| 5. Alkyl/polyether co-modified silicone[2] | 1.0 |
| 6. Acrylic silicone resin[3] | 15.0 |
| 7. Iron oxide black treated with organopolysiloxane[4] | 20.0 |
| 8. Ethanol | 5.0 |
| 9. Antiseptics | q.s. |
| 10. Purified water | balance |

[1]Polyether-modified silicone; KF6017 from Shin-Etsu Chemical Co., Ltd.
[2]Alkyl/polyether co-modified silicone; KF6038 from Shin-Etsu Chemical Co., Ltd.
[3]Acrylic silicone resin; KP545 from Shin-Etsu Chemical Co., Ltd.
[4]In the method as described above, 98 parts by weight of iron oxide black powder was treated with 2 parts by weight of 1/1 mixture in weight of the organopolysiloxane of the Prepartaion Example 1 and that of the Preparation Example 2.

Preparation Procedures

A: Components 1 to 6 were mixed, to which component 7 was added and mixed.

B: Components 8 to 10 were mixed.

C: The mixture obtained in B was added to the mixture obtained in A and emulsified by stirring.

The eyeliner thus obtained had non-powdery texture and good stability. It spread lightly and gave refreshing and moisturized feel to the skin The applied eyeliner was resistant to water and sweat, and durable.

Example 22

Powder Eyebrow

| Component | Wt % |
|---|---|
| 1. Vseline | 2.5 |
| 2. Dimethylpolysiloxane (6 mm$^2$/sec at 25° C.) | 1.5 |
| 3. Alkyl-modified crosslinked polyether-modified silicone[1] | 1.5 |
| 4. Glyceryl trioctanoate | 3.0 |
| 5. Mica treated with organopolysiloxane[2] | 40.0 |
| 6. Talc treated with organopolysiloxane[2] | balance |
| 7. Titanium treated with organopolysiloxane[2] | 10.0 |
| 8. Barium treated with organopolysiloxane[2] | 15.0 |
| 9. Iron oxide treated with organopolysiloxane[2] | q.s. |
| 10. Composite powder of hybrid silicone[3] | 1.5 |
| 11. Polymethylsilsesquioxane Spherical powder[4] | 2.5 |
| 12. Antiseptics | 2.5 |
| 13. Perfume | q.s. |

[1]Alkyl-modified crosslinked polyether-modified silicone; KSG-41 from Shin-Etsu Chemical Co., Ltd.
[2]Two parts by weight of the powder was treated with 98 parts by weight of the 1/1 mixture of the organopolysiloxane prepared in the Preparation Example 1 and the organopolysiloxane prepared in the Preparation Example 2 in the same manner described above.
[3]Composite powder of hybrid silicone, KSP-100 from Shin-Etsu Chemical Co., Ltd.
[4]Polymethylsilsesquioxane Spherical powder, KMP-590 from Shin-Etsu Chemical Co., Ltd.

Preparation Procedures

A: Components 5 to 12 were mixed.

B: Components 1 to 4 were mixed and the mixture obtained was added to the mixture from A.

C: To the mixture obtained in B, component 13 was added and pressed in a metal mold.

The powder eyebrow obtained was stable with time, spread lightly and gave refreshing feel with no stickiness. The applied eyebrow had good affinity to the skin and resistance to water and sweat to be durable.

Example 23

Eye Shadow

| Component | Weight (%) |
|---|---|
| 1. Sericite (Example 3) | 40.0 |
| 2. Mica treated with organopolysiloxane[1] | 10.0 |
| 3. Talc treated with organopolysiloxane[1] | balance |
| 4. Titanium treated with organopolysiloxane[1] | 10.0 |
| 5. Titanium oxide fine powder (Example 1) | 5.0 |
| 6. Magnesium stearate | 3.0 |
| 7. Pigment | q.s. |
| 8. Octyl decanol | 3.0 |
| 9. Dimethylpolysiloxane (6 mm$^2$/sec at 25° C.) | 4.0 |
| 10. Crosslinked dimethylpolysiloxane[2] | 6.0 |
| 11. Antiseptics | q.s. |
| 12. Perfume | q.s. |

[1]In the method as described above, 98 parts by weight of the powder was treated with 2 parts by weight of the 1/2, in weight ratio, mixture of the organopolysiloxane prepared in the Preparation Example 1 and the organopolysiloxane prepared in the Preparation Example 2.
[2]Crosslinked dimethylpolysiloxane, KSG-16 from Shin-Etsu Chemical Co., Ltd.

A: Components 8 to 11 were mixed.

B: Components 1 to 7 were mixed and the mixture obtained was added to the mixture from A.

C: To the mixture obtained in B, component 12 was added.

The eye shadow obtained was stable with time, spread lightly and gave refreshing feel to the skin with no stickiness. The applied eye shadow had good affinity to the skin, and was glossy and durable.

Example 24

Eye Shadow

| Component | Weight (%) |
|---|---|
| 1. Decamethylcyclopentasiloxane | 15.0 |
| 2. Dimethylpolysiloxane (6 mm$^2$/sec at 25° C.) | 10.0 |
| 3. Branched polyether-modified silicone[1] | 2.5 |
| 4. Chromium treated with organopolysiloxane[1] | 6.5 |
| 5. Ultramarine blue pigment[2] | 4.0 |
| 6. Mica coated with titanium treated with organopolysiloxane[2] | 6.0 |
| 7. Sodium chloride | 2.0 |
| 8. Propyleneglycol | 8.0 |
| 9. Antiseptics | q.s. |
| 10. Perfume | q.s. |
| 11. Purified water | 46.0 |

[1]Branched polyether-modified silicone: KF-6028 from Shin-Etsu Chemical Co., Ltd.
[2]In the same manner as described above, 98 parts by weight of the powder was treatedwith 2 parts by weight of the 1/1 mixture of the organopolysiloxane prepared in the Preparation Example 1 and the organopolysiloxane prepared in the Preparation Example 3.

Preparation Procedures

A: Components 1 to 3 were mixed, to which components 4-6 were added.

B: Components 7 to 9 and 11 were mixed.

C: While stirring, the mixture obtained in B was added to the mixture obtained in A and emulsified, to which component 10 was added.

The eye shadow obtained had non-powdery texture and good stability. It spread lightly and gave refreshing feel with no oiliness to the skin. The applied eye shadow was resistant to water and sweat, and durable.

Example 25

Stick Eye Shadow

| Component | Weight (%) |
| --- | --- |
| 1. Ethylene glycol distearate | 12.0 |
| 2. Crosslinked methylphenylpolysiloxane[1] | 5.0 |
| 3. Isotridecyl isononanate | 35.0 |
| 4. candelilla wax | 8.0 |
| 5. Lecithin | 0.2 |
| 6. Composite powder of hybrid silicone[2] | 4.0 |
| 7. Iron oxide red treated with organopolysiloxane[3] | 6.2 |
| 8. Mica coated with titanium treated with organopolysiloxane[3] | balance |

[1] Crosslinked methylphenylpolysiloxane, KSG-18 from Shin-Etsu Chemical Co., Ltd.
[2] Composite powder of hybrid silicone, KSP-100 from Shin-Etsu Chemical Co., Ltd.
[3] In the same manner as described above, 98 parts by weight of the powder was treated with 2 parts by weight of the 1/1 mixture of the organopolysiloxane prepared in the Preparation Example 1 and the organopolysiloxane prepared in the Preparation Example 3.

Preparation Procedures

A: Components 2 and 3 were mixed.
B: Components 1, 4 and 5 were mixed while heating, to which the mixture obtained in A was added.
C: Components 6-8 were mixed.
D: The mixture obtained in C was added to the mixture obtained in B and poured in a mold.

The stick eye shadow obtained had non-powdery texture and good stability. It spread lightly and gave refreshing feel with no oiliness to the skin. The applied eye shadow was resistant to water and sweat, and durable.

Example 26

Cream Eye Shadow

| Component | Weight (%) |
| --- | --- |
| 1. Acrylic silicone resin[1] | 10.0 |
| 2. Acrylic silicone resin having a long alkyl chain[2] | 2.0 |
| 3. Branched polyether-modified silicone[3] | 1.5 |
| 4. Decamehtylcyclopentasiloxane | 20.3 |
| 5. Cetyl isooctanoate | 3.0 |
| 6. Organic modified bentnite | 1.2 |
| 7. Polyamide (Nylon) | 3.0 |
| 8. Talc treated with organopolysiloxane[4] | 4.0 |
| 9. Iron oxide treated with organopolysiloxane[5] | 20.0 |
| 10. Ethanol | 5.0 |
| 11. Antiseptics | q.s. |
| 12. Purified water | 30.0 |

[1] Acrylic silicone resin: KP-545 from Shin-Etsu Chemical Co., Ltd.
[2] Acrylic silicone resin having a long alkyl chain: KP-561P from Shin-Etsu Chemical Co., Ltd.
[3] Branched polyether-modified silicone: KF-6028 from Shin-Etsu Chemical Co., Ltd.
[4] In the same manner as described above, 98 parts by weight of the powder was treated with 2 parts by weight of the 1/1 mixture of the organopolysiloxane prepared in the Preparation Example 1 and the organopolysiloxane prepared in the Preparation Example 2.
[5] In the same manner as described above, 98 parts by weight of the powder was treated with 2 parts by weight of the 1/1 mixture of the organopolysiloxane prepared in the Preparation Example 1 and the organopolysiloxane prepared in the Preparation Example 3.

Preparation Procedures

A: Components 1 to 6 were mixed, to which components 7 to 9 were added and dispersed.
B: Components 10 to 12 were mixed.
C: While stirring, the mixture obtained in B was added to the mixture obtained in A and emulsified.

The cream eye shadow stick obtained had non-powdery texture and good stability. It spread lightly and gave refreshing feel with no oiliness to the skin. The applied cream eye shadow had good affinity to eyelids was resistant to water and sweat, and durable.

Example 27

Lipstick

| Component | Weight (%) |
| --- | --- |
| 1. candelilla wax | 8.0 |
| 2. Polyethylene wax | 8.0 |
| 3. Acrylic silicone resin having a long alkyl chain[1] | 12.0 |
| 4. Methylphenylpolysiloxane[2] | 3.0 |
| 5. Isotridecyl isononanate | 20.0 |
| 6. Glyceryl isostearate | 16.0 |
| 7. Polyglyceryl triisostearate | 28.5 |
| 8. Red No. 202 treated with organopolysiloxane[3] | 0.8 |
| 9. Iron oxide red treated with organopolysiloxane[3] | 1.5 |
| 10. Iron oxide yellow treated with organopolysiloxane[3] | 1.0 |
| 11. Iron oxide black treated with organopolysiloxane[3] | 0.2 |
| 12. Titanium oxide treated with organopolysiloxane[3] | 1.0 |
| 13. Antiseptics | q.s. |
| 14. Perfume | q.s. |

[1] Acrylic silicone resin having a long alkyl chain: KP-561P from Shin-Etsu Chemical Co., Ltd.
[2] Methylphenylpolysiloxane: KF-54 from Shin-Etsu Chemical Co., Ltd.
[3] In the same manner as described above, 98 parts by weight of the powder was treated with 2 parts by weight of the 1/1 mixture of the organopolysiloxane prepared in the Preparation Example 1 and the organopolysiloxane prepared in the Preparation Example 2.

Preparation Procedures

A: Components 1 to 6 were mixed and part of component 7 was mixed to dissolve.
B: Components 8 to 14 and the rest of the component 7 were mixed homogeneously and the resulting mixture was added to A to obtain a homogenous mixture.

The lipstick thus obtained had a non-powdery texture and good stability. It spread lightly and gave refreshing feel. Applied lipstick had glossy appearance and durable with goof resistant to water.

Example 28

Liquid Lipstick

| Component | Weight (%) |
| --- | --- |
| 1. Palmitic acid/dextrin ethylhexanoate[1] | 7.0 |
| 2. Glyceryl trioctanoate | 12.0 |
| 3. Alkyl-modified dimethylpolysiloxane[2] | 6.0 |
| 4. Branched alkyl/polyglycerin co-modified silicone[3] | 2.0 |
| 5. Decamethylcyclopentasiloxane | 34.0 |
| 6. Dipropylene glycol | 4.0 |
| 7. Antiseptics | q.s. |
| 8. Purified water | 16.0 |
| 9. Polyglyceryl triisostearate | 5.4 |
| 10. Sericite treated with organopolysiloxane (Example 4) | 1.0 |
| 11. Red No. 201 treated with organopolysiloxane[4] | 0.2 |
| 12. Red No. 202 treated with organopolysiloxane[4] | 0.5 |
| 13. Yellow No. 4 aluminum lake treated with organopolysiloxane[4] | 1.6 |
| 14. Iron oxide red treated with organopolysiloxane[4] | 1.0 |
| 15. Iron oxide black treated with organopolysiloxane[4] | 0.3 |

-continued

| Component | Weight (%) |
|---|---|
| 16. Titanium treated with organopolysiloxane[4] | 4.0 |
| 17. Mica | 5.0 |
| 18. Perfume | q.s |

[1] Palmitic acid/dextrin ethylhexanoate: Rheopearl TT, ex Chiba Seihun Co.
[2] Alkyl-modified dimethylpolysiloxane: KSG-43 from Shin-Etsu Chemical Co., Ltd.
[3] Branchedalkyl/polyglycerin co-modifiedsilicone: KF-6105 from Shin-Etsu Chemical Co., Ltd.
[4] In the same manner as described above, 98 parts by weight of the powder was treated with 2 parts by weight of the 1/1 mixture of the organopolysiloxane prepared in the Preparation Example 1 and the organopolysiloxane prepared in the Preparation Example 3.

Preparation Procedures

A: Components 1 to 5 were mixed, while heating.
B: Components 6 to 8 were mixed and heated.
C: Components 10 to 16 were mixed, to which component 9 was added.
D: The mixture obtained in B was added to the mixture obtained in A and emulsified. The emulsion obtained was added to the mixture obtained in C, to which components 17 and 18 were added. The mixture obtained was poured in a mold and cooled.

The lipstick thus obtained had a non-powdery texture and good stability. It spread lightly and gave refreshing feel without oiliness. Applied lipstick had glossy appearance and durable.

Example 29

Lipstick

| Component | Weight (%) |
|---|---|
| 1. Candelilla wax | 3.5 |
| 2. Polyethylene wax | 2.0 |
| 3. Microcrystalline wax | 3.0 |
| 4. Ceresin wax | 5.5 |
| 5. Acrylic silicone resin having a long alkyl chain[1] | 13.0 |
| 6. Branched alkyl/polyglycerin co-modified silicone[2] | 3.0 |
| 7. Macadamia nut oil | 20.0 |
| 8. Diisosteary malate | 8.0 |
| 9. Hydrogenated polyisobutene | 8.0 |
| 10. Isotridecyl isononanate | 15.0 |
| 11. Polyglyceryl triisostearate | 5.4 |
| 12. Sericite treated with organopolysiloxane (Example 3) | 1.0 |
| 13. Red No. 201 treated with organopolysiloxane[3] | 0.2 |
| 14. Red No. 202 treated with organopolysiloxane[3] | 0.5 |
| 15. Yellow No. 4 aluminum lake treated with organopolysiloxane[3] | 1.6 |
| 16. Iron oxide red treated with organopolysiloxane[3] | 1.0 |
| 17. Iron oxide black treated with organopolysiloxane[3] | 0.3 |
| 18. Titanium oxide treated with organopolysiloxane[3] | 4.0 |
| 19. Mica | 5.0 |
| 20. Antiseptics | q.s. |
| 21. Perfume | q.s. |

[1] Acrylic silicone resin having a long alkyl chain: KP-561P from Shin-Etsu Chemical Co., Ltd.
[2] Branched alkyl/polyglycerin co-modified silicone: KF-6105 from Shin-Etsu Chemical Co., Ltd.
[3] In the method as described above, 98 parts by weight of the powder was treated with 2 parts by weight of the 1/1 mixture of the organopolysiloxane prepared in the Preparation Example 1 and the organopolysiloxane prepared in the Preparation Example 2.

Preparation Procedures

A: Components 1 to 10 and 20 were mixed, while heating.
B: Components 12 to 18 and 11 were mixed and added to the mixture obtained in A.
C: To the mixture obtained in B, components 19 and 21 were added and poured in a mold and cooled.

The lipstick thus obtained had a non-powdery texture and good stability. It spread lightly and adhered well on the lip by taking in water, so that the applied lipstick was very durable and had glossy appearance.

Example 30

Lipstick

| Component | Weight (%) |
|---|---|
| 1. Candelilla wax | 3.5 |
| 2. Polyethylene wax | 2.0 |
| 3. Microcrystalline wax | 3.0 |
| 4. Ceresin wax | 5.5 |
| 5. Acrylic silicone resin having a long alkyl chain[1] | 13.0 |
| 6. Crosslinked alkyl/polyether co-modified silicone[2] | 3.0 |
| 7. Macadamia nut oil | 20.0 |
| 8. Diisosteary malate | 8.0 |
| 9. Hydrogenated polyisobutene | 8.0 |
| 10. Isotridecyl isononanate | 15.0 |
| 11. Polyglyceryl triisostearate | 5.4 |
| 12. Sericite treated with organopolysiloxane (Example 4) | 1.0 |
| 13. Red No. 201 treated with organopolysiloxane[3] | 0.2 |
| 14. Red No. 202 treated with organopolysiloxane[3] | 0.5 |
| 15. Yellow No. 4 aluminum lake treated with organopolysiloxane[3] | 1.6 |
| 16. Iron oxide red treated with organopolysiloxane[3] | 1.0 |
| 17. Iron oxide black treated with organopolysiloxane[3] | 0.3 |
| 18. Titanium oxide treated with organopolysiloxane[3] | 4.0 |
| 19. Mica | 5.0 |
| 20. Antiseptics | q.s. |
| 21. Perfume | q.s. |

[1] Acrylic silicone resin having a long alkyl chain: KP-561P from Shin-Etsu Chemical Co., Ltd.
[2] Crosslinked alkyl/polyether co-modified silicone: KSG-330 from Shin-Etsu Chemical Co., Ltd.
[3] In the method as described above, 98 parts by weight of the powder was treated with 2 parts by weight of the 1/1 mixture of the organopolysiloxane prepared in the Preparation Example 1 and the organopolysiloxane prepared in the Preparation Example 3.

Preparation Procedures

A: Components 1 to 10 and 20 were mixed, while heating.
B: Components 12 to 18 and 11 were mixed and added to the mixture obtained in A.
C: To the mixture obtained in B, components 19 and 21 were added and poured in a mold and cooled.

The lipstick thus obtained had a non-powdery texture and good stability. It spread lightly and adhered well on the lip by taking in water, so that the applied lipstick was very durable and had glossy appearance.

Example 31

Long-Lasting Lipstick

| Component | Weight (%) |
|---|---|
| 1. Candelilla wax | 8.0 |
| 2. Polyethylene wax | 5.0 |
| 3. Microcrystalline wax | 1.0 |
| 4. Acrylic silicone resin having a long alkyl chain[1] | 8.0 |
| 5. Macadamia nut oil | 6.0 |
| 6. Diisosteary malate | 1.0 |
| 7. Isotridecyl isononanate | 4.0 |
| 8. Acrylic silicone resin[2] | 45.0 |
| 9. Tetramethylcyclopentasiloxane | 3.0 |
| 10. Polyglyceryl triisostearate | 5.4 |
| 11. Sericite treated with organopolysiloxane (Example 4) | 1.0 |
| 12. Red No. 201 treated with organopolysiloxane[3] | 0.2 |

-continued

| Component | Weight (%) |
|---|---|
| 13. Red No. 202 treated with organopolysiloxane[3] | 0.5 |
| 14. Yellow No. 4 aluminum lake treated with organopolysiloxane[3] | 1.6 |
| 15. Iron oxide red treated with organopolysiloxane[3] | 1.0 |
| 16. Iron oxide black treated with organopolysiloxane[3] | 0.3 |
| 17. Titanium oxide treated with organopolysiloxane[3] | 4.0 |
| 18. Mica | 5.0 |
| 19. Antiseptics | q.s. |
| 20. Perfume | q.s. |

[1]Acrylic silicone resin having a long alkyl chain: KP-561P from Shin-Etsu Chemical Co., Ltd.
[2]Acrylic silicone resin: KP-545 from Shin-Etsu Chemical Co., Ltd.
[3]In the method as described above, 98 parts by weight of the powder was treated with 2 parts by weight of the 1/1 mixture of the organopolysiloxane prepared in the Preparation Example 1 and the organopolysiloxane prepared in the Preparation Example 3.

Preparation Procedures

A: Components 1 to 7 and 19 were mixed and heated.

B: Components 11 to 17 and 10 were mixed and added to the mixture obtained in A.

C: To the mixture obtained in B, components 8, 9 and 20 were added and poured in a sealable container.

The lipstick thus obtained had a non-powdery texture and good stability. It spread lightly on the lip. Applied lipstick had glossy appearance and adhered well to the lips after the volatile oil agents evaporated. Applied lipstick was very durable and resistant to water.

Example 32

Foundation

| Component | Weight (%) |
|---|---|
| 1. Decamethylcyclopentasiloxane | 45.0 |
| 2. Dimethylpolysiloxane (6 mm$^2$/sec at 25° C.) | 5.0 |
| 3. Branched polyether-modified silicone[1] | 2.0 |
| 4. Organic-modified bentnite | 4.0 |
| 5. Titanium treated with organopolysiloxane[2] | 10.0 |
| 6. Talc treated with organopolysiloxane[2] | 6.0 |
| 7. Mica treated with organopolysiloxane[2] | 6.0 |
| 8. Iron oxide red treated with organopolysiloxane[2] | 1.6 |
| 9. Iron oxide yellow treated with organopolysiloxane[2] | 0.7 |
| 10. Iron oxide black treated with organopolysiloxane[2] | 0.2 |
| 11. Dipropylene glycol | 5.0 |
| 12. Methyl paraoxybenzoate | 0.3 |
| 13. 2-amino-2-methyl-1,3-propanediol | 0.2 |
| 14. Hydrochloric acid | 0.1 |
| 15. Perfume | q.s. |
| 16. Purified water | balance |

[1]Branched polyether-modified silicone[1]: KF-6028 from Shin-Etsu Chemical Co., Ltd.
[2]In the method as described above, 98 parts by weight of the powder was treated with 2 parts by weight of the 1/2 mixture of the organopolysiloxane prepared in the Preparation Example 1 and the organopolysiloxane prepared in the Preparation Example 2.

Preparation Procedures

A: Components 1 to 4 were mixed, to which components 5 to 10 were mixed.

B: Components 11 to 14 were dissolved in component 16. The solution obtained had a pH of 9.0.

C: While stirring, the mixture obtained in A was added to the solution obtained in B and emulsified, to which component 15 was added.

The foundation thus obtained had a fine texture and good stability. It spread lightly on the skin and gave refreshing feel with no stickiness. Applied foundation was durable with good resistant to sweat and sebum.

Example 33

Powder Foundation

| Component | Wt % |
|---|---|
| 1. Vseline | 2.0 |
| 2. Squalane | 2.0 |
| 3. Dimethylpolysiloxane (20 mm$^2$/sec at 25° C.) | 3.0 |
| 4. Polyethylene powder | 1.5 |
| 5. Sericite treated with organopolysiloxane(Example 3) | 1.0 |
| 6. Barium sulfate | 8.5 |
| 7. Titanium treated with organopolysiloxane[1] | 9.0 |
| 8. Composite powder of phenyl-modified hybrid silicone[2] | 3.0 |
| 9. Polymethylsilsesquioxane spherical powder[3] | 4.5 |
| 10. Talc treated with organopolysiloxane[1] | 25.0 |
| 11. Iron oxide red treated with organopolysiloxane[1] | 0.4 |
| 12. Iron oxide yellow treated with organopolysiloxane[1] | 1.0 |
| 13. Iron oxide black treated with organopolysiloxane[1] | 0.1 |
| 14. Antiseptics | q.s. |
| 15. Perfume | q.s. |

[1]In the method as described above, 98 parts by weight of the powder was treated with 2 parts by weight of the 1/2 mixture of the organopolysiloxane prepared in the Preparation Example 1 and the organopolysiloxane prepared in the Preparation Example 2.
[2]Composite powder of phenyl-modified hybrid silicone: KSP-300 from Shin-Etsu Chemical Co., Ltd.
[3]Polymethylsilsesquioxane spherical powder: KMP-590 from Shin-Etsu Chemical Co., Ltd.

Preparation Procedures

A: Components 1 to 3 were mixed.

B: Components 4 to 14 were mixed.

C: The mixture obtained in B was added to the mixture obtained in A and component 15, which was pressed in a container.

The foundation thus obtained had a non-powdery texture and good stability. It spread lightly on the skin and gave refreshing feel with no stickiness. Applied foundation was durable with good resistant to sweat and sebum.

Example 34

Emulsified Foundation

| Component | Weight (%) |
|---|---|
| 1. Dimethylpolysiloxane (6 mm$^2$/sec (25° C.)) | 4.5 |
| 2. Decamethylcyclopentasiloxane | 15.0 |
| 3. Squalane | 4.0 |
| 4. Neopentylglycol dioctanoate | 3.0 |
| 5. Myristic acid isostearic acid diglyceride | 2.0 |
| 6. α-monoisostearyl glyceryl ether | 1.0 |
| 7. Polyether-modified silicone[1] | 1.0 |
| 8. Alkyl/polyether co-modified silicone[2] | 0.5 |
| 9. Titanium oxide treated with organopolysiloxane[3] | 5.0 |
| 10. Sericite treated with organopolysiloxane[3] | 2.0 |
| 11. Talc treated with organopolysiloxane[3] | 3.0 |
| 12. Iron oxide red treated with organopolysiloxane[3] | 0.4 |
| 13. Iron oxide yellow treated with organopolysiloxane[3] | 0.7 |
| 14. Iron oxide black treated with organopolysiloxane[3] | 0.1 |
| 15. Magnesium sulfate | 0.8 |
| 16. Glycerin | 3.0 |

-continued

| Component | Weight (%) |
|---|---|
| 17. Antiseptics | q.s. |
| 18. Perfume | q.s. |
| 19. Purified water | balance |

[1] Polyehter-modifeid silicone; KF6017 from Shin-Etsu Chemical Co., Ltd.
[2] Alkyl/polyether co-modified silicone; KF6105 from Shin-Etsu Chemical Co., Ltd.
[3] In the method as described above, 98 parts by weight of powder was treated with 2 parts by weight of 1/2 mixture of the organopolysiloxane of the Preparation Example 1 and the organopolysiloxane of the Preparation Example 2.

Preparation Procedures

A: Components 4 and 8 were mixed, to which components 9-14 were added and dispersed.
B: Components 1 to 3 and 5 to 7 were mixed.
C: Components 15 to 17 and 19 were mixed.
D: While stirring, the mixture obtained in A was added to the mixture obtained by B, to which the mixture obtained in C was added and emulsified. To the emulsion thus obtained, component 18 was added.

The emulsified foundation thus obtained had a low viscosity, a fine texture, and good stability. It spread lightly on the skin to gave moisturized and refreshing feel. The applied foundation was resistant to sweat and durable.

Example 35

Liquid Foundation

| Component | Weight(%) |
|---|---|
| 1. Decamethylcyclopentasiloxane | 16.0 |
| 2. Dimethylpolysiloxane (6 mm$^2$/sec (25° C.)) | 8.0 |
| 3. Octyl paramethoxycinnamate | 3.0 |
| 4. 12-Hydroxystearic acid | 1.0 |
| 5. Fluorine-modified silicone[1] | 15.0 |
| 6. Fluorinated alkyl/polyether co-modified silicone[2] | 5.0 |
| 7. Powder of spherical polymethylsilsesquioxane[3] | 3.0 |
| 8. Fine powder of titanium oxide treated with organopolysiloxane (Example 2) | 8.0 |
| 9. Mica titanium oxide treated with organopolysiloxane[4] | 1.0 |
| 10. Titanium oxide treated with organopolysiloxane[4] | 5.0 |
| 11. Iron oxide red treated with organopolysiloxane[4] | 0.9 |
| 12. Iron oxide yellow treated with organopolysiloxane[4] | 2.0 |
| 13. Iron oxide black treated with organopolysiloxane[4] | 1.0 |
| 14. Ethanol | 15.0 |
| 15. Glycerin | 3.0 |
| 16. Magnesium sulfate | 1.0 |
| 17. Antiseptics | q.s. |
| 18. Perfume | q.s. |
| 19. Purified water | balance |

[1] Fluorine-modified silicone; FL-50 from Shin-Etsu Chemical Co., Ltd.
[2] Flourinated alkyl/polyether-comodified silicone; FPD-4694 from Shin-Etsu Chemical Co., Ltd.
[3] Powder of spherical polymethylsilsesquioxane; KMP 590 from Shin-Etsu Chemical Co., Ltd.
[4] In the method as described above, 98 parts by weight of powder was treated with 2 parts by weight of 1/1 mixture of the organopolysiloxane of the Preparation Example 1 and the organopolysiloxane of the Preparation Example 3.

Preparation Procedures

A: Components 7 to 13 were mixed.
B: Components 1 to 6 were mixed while heating to 70° C. and the mixture obtained in A was added and dispersed.
C: Components 14 to 17 and component 19 were mixed and heated to 40° C.
D: The mixture obtained in C was added to the emulsion obtained in B. The resulting mixture was emulsified and cooled, to which component 18 was added.

The liquid emulsified foundation thus obtained was stable with time and spread lightly on the skin to give refreshing feel. The applied foundation was resistant to sweat and durable.

Example 36

Oil-in-Water Type Liquid Foundation

| Component | Wt % |
|---|---|
| 1. Stearic acid | 1.0 |
| 2. Behenyl alcohol | 0.4 |
| 3. Gryceryl stearate | 0.3 |
| 4. Liquid paraffin | 10.0 |
| 5. Glyceryl trioctanoate | 5.0 |
| 6. Acrylic/silicone resin having a long alkyl chain[1] | 3.0 |
| 7. Sorbitan sesquioleate | 0.5 |
| 8. Sorbitan monooleate | 1.0 |
| 9. Acryl/alkyl copolymer | 2.2 |
| 10. Triethanolamine | 1.0 |
| 11. Ethanol | 3.0 |
| 12. Composite powder of hybrid silicone[2] | 3.0 |
| 13. Polyether-modified silicone[3] | 0.2 |
| 14. Alkyl/POE castor oil | 0.1 |
| 15. POE hydrogenated castor oil | 0.5 |
| 16. Titanium oxide treated with organopolysiloxane[4] | 8.5 |
| 17. Iron oxide red treated with organopolysiloxane[4] | 0.4 |
| 18. Iron oxide yellow treated with organopolysiloxane[4] | 1.0 |
| 19. Iron oxide black treated with organopolysiloxane[4] | 0.1 |
| 20. 1,3-butylene glycol | 7.0 |
| 21. Antiseptics | q.s. |
| 22. Perfume | q.s. |
| 23. Purified water | 51.8 |
| HYDROGENATED CASTOR OIL | |

[1] Acrylic/silicone resin having a long alkyl chain: KP-561P from Shin-Etsu Chemical Co., Ltd.
[2] Composite powder of hybrid silicone: KSP-100 from Shin-Etsu Chemical Co., Ltd.
[3] Polyether-modified silicone: KF-6013 from Shin-Etsu Chemical Co., Ltd.
[4] In the method as described above, 98 parts by weight of powder was treated with 2 parts by weight of 1/1 mixture of the organopolysiloxane of the Preparation Example 1 and the organopolysiloxane of the Preparation Example 2.

Preparation Procedures

A: Components 13 to 15 and a part of component 20 were mixed, to which components 16-19 were added and heated.
B: Components 1 to 8 were mixed while heating to form a solution.
C: Components 9, 10, the remaining part of components 20, 21 and 23 were mixed and heated.
D: Components 11 and 12 were mixed.
E: While stirring, the solution obtained in B was added to the mixture obtained in A, to which the mixture obtained in D and component 22 were added.

The oil-in-water type liquid foundation thus obtained had a fine texture and was stable with time. It spread lightly on the skin to give refreshing feel. The applied foundation was resistant to water and sweat, and durable.

Example 37

Oil-in-Water Type Cream Foundation

| Component | wt % |
|---|---|
| 1. Crosslinked dimethylpolysiloxane[1] | 7.0 |
| 2. Crosslinked dimethylpolysiloxane[2] | 25.0 |
| 3. Acrylic silicone resin[3] | 10.0 |

-continued

| Component | wt % |
|---|---|
| 4. Branched polyglycerin-modified silicone[4] | 0.9 |
| 5. Branched polyglycerin-modified silicone[5] | 0.3 |
| 6. Alkkyl/polyglycerin co-modified silicone[6] | 0.1 |
| 7. POE hydrogenated castor oil | 0.3 |
| 8. Titanium oxide treated with organopolysiloxane[7] | 8.5 |
| 9. Iron oxide red treated with organopolysiloxane[7] | 0.4 |
| 10. Iron oxide yellow treated with organopolysiloxane[7] | 1.0 |
| 11. Iron oxide black treated with organopolysiloxane[7] | 0.1 |
| 12. 1,3-butylene glycol | 5.0 |
| 13. Polyacrylamide emulsifier | 1.6 |
| 14. Ammonium acryloyldimethyltaulin/VP copolymer (5% aqueous solution) | 12.0 |
| 15. Sodium chloride | 0.1 |
| 16. Antiseptics | q.s. |
| 17. Perfume | q.s. |
| 18. Purified water | 27.7 |

[1]Crosslinked dimethylpolysiloxane; KSG-15 from Shin-Etsu Chemical Co., Ltd.
[2]Crosslinked dimethylpolysiloxane; KSG-16 from Shin-Etsu Chemical Co., Ltd.
[3]Acrylic silicone resin; KP-545 from Shin-Etsu Chemical Co., Ltd.
[4]Branched polyglycerin-modified silicone; KF-6100 from Shin-Etsu Chemical Co., Ltd.
[5]Branched polyglycerin-modified silicone; KF-6104 from Shin-Etsu Chemical Co., Ltd.
[6]Alkkyl/polyglycerin co-modified silicone; KF-6105 from Shin-Etsu Chemical Co., Ltd.
[7]In the method as described above, 98 parts by weight of powder was treated with 2 parts by weight of 1/1 mixture of the organopolysiloxane of the Preparation Example 1 and the organopolysiloxane of the Preparation Example 2.

Preparation Procedures

A: Components 6, 7, 12 and a part of component 4 were mixed, to which components 8-11 were added. The mixture obtained was dispersed in a part of component 18.

B: Components 1 to 3 were mixed.

C: The remaining part of component 4, components 5, 13-16, and the remaining part of component 8 were mixed and heated.

D: While stirring, the mixture obtained in B was added to the mixture obtained in C and emulsified, to which the dispersion obtained in A and component 17 were added.

The oil-in-water type cream foundation thus obtained had a fine texture and was stable with time. It spread lightly on the skin to give smooth, non-sticky, moisturized finish, which was resistant to water and sweat, and durable.

Example 38

Water-in-Oil Type Liquid Foundation

| Component | wt % |
|---|---|
| 1. Crosslinked polyether-modified silicone[1] | 3.5 |
| 2. Crosslinked dimethylpolysiloxane[2] | 5.0 |
| 3. Branched polyether-modified silicone[3] | 2.0 |
| 4. Organic-modified bentnite | 1.2 |
| 5. Glyceryl trioctanoate | 5.0 |
| 6. Dimethylpolysiloxane (6 mm$^2$/sec(25° C.)) | 6.5 |
| 7. Decamethylcyclosiloxane | 13.6 |
| 8. Acrylic silicone resin containing acrylic acid[4] | 1.5 |
| 9. Titanium oxide treated with organopolysiloxane[5] | 8.5 |
| 10. Iron oxide red treated with organopolysiloxane[5] | 0.4 |
| 11. Iron oxide yellow treated with organopolysiloxane[5] | 1.0 |
| 12. Iron oxide black treated with organopolysiloxane[5] | 0.1 |
| 13. Titanimu oxide fine powder dispersion[6] | 10.0 |
| 14. 1,3-butyleneglycol | 5.0 |
| 15. Sodium citrate | 0.2 |
| 16. Sodium chloride | 0.5 |
| 17. Antiseptics | q.s. |
| 18. Perfume | q.s. |
| 19. Purified water | 36.0 |

[1]Crosslinked polyether-modified silicone; KSG-210 from Shin-Etsu Chemical Co., Ltd.
[2]Crosslinked dimethylpolysiloxane; KSG-15 from Shin-Etsu Chemical Co., Ltd.
[3]Branched polyether-modified silicone; KF-6028 from Shin-Etsu Chemical Co., Ltd.
[4]Acrylic silicone resin containing acrylic acid; KP-575 from Shin-Etsu Chemical Co., Ltd.
[5]In the method as described above, 98 parts by weight of powder was treated with 2 parts by weight of 1/1 mixture of the organopolysiloxane of the Preparation Example 1 and the organopolysiloxane of the Preparation Example 2.
[6]Titanium oxide fine powder dispersion; SPD-T5 from Shin-Etsu Chemical Co., Ltd.

Preparation Procedures

A: A part of component 7 was mixed with component 8, to which components 9-12 were mixed and dispersed.

B: Components 1 to 6, and the remaining part of component 7 were mixed.

C: Components 14-17 and 19 were mixed.

D: While stirring, the mixture obtained in B was added to the mixture obtained in C and emulsified, to which the dispersion obtained in A and component 18 were added.

The water-in-oil type liquid foundation thus obtained had a fine texture and was stable with time. It spread lightly on the skin to give moisturized finish. The cosmetic film formed was beautiful, resistant to water and sweat, and durable.

Example 39

Water-in-Oil Type Cream Foundation

| Component | wt % |
|---|---|
| 1. Alkyl-modified crosslinked polyether-modified silicone[1] | 2.0 |
| 2. Alkyl-modified crosslinked dimethylpolysiloxane[2] | 2.0 |
| 3. Branched alkyl/polyether co-modified silicone[3] | 1.0 |
| 4. Liquid paraffin | 2.0 |
| 5. Glyceryl trioctanoate | 5.0 |
| 6. Isotridecyl isononanate | 9.0 |
| 7. POE hydrogenated castor oil | 0.3 |
| 8. Branched polyglycerin-modified silicone[4] | 0.3 |
| 9. Branched alkyl/polyglycerin co-modified silicone[5] | 0.1 |
| 10. Composite powder of hybrid silicone[6] | 2.0 |
| 11. Titanium oxide treated with organopolysiloxane[7] | 8.5 |
| 12. Iron oxide red treated with organopolysiloxane[7] | 0.4 |
| 13. Iron oxide yellow treated with organopolysiloxane[7] | 1.0 |
| 14. Iron oxide black treated with organopolysiloxane[7] | 0.1 |
| 15. 1,3-butyleneglycol | 5.0 |
| 16. Sodium citrate | 0.2 |
| 17. Sodium chloride | 0.5 |
| 18. Antiseptics | q.s. |
| 19. Perfume | q.s. |
| 20. Purified water | 60.6 |

[1]Alkyl-modified crosslinked polyether-modified silicone; KSG-310 from Shin-Etsu Chemical Co., Ltd.
[2]Alkyl-modified crosslinked dimethylpolysiloxane; KSG-41 from Shin-Etsu Chemical Co., Ltd.
[3]Branched alkyl/polyether co-modified silicone; KF-6038 from Shin-Etsu Chemical Co., Ltd.
[4]Branched polyglycerin-modified silicone; KF-6100 from Shin-Etsu Chemical Co., Ltd.
[5]Branched alkyl/polyglycerin co-modified silicone; KF-6105 from Shin-Etsu Chemical Co., Ltd.
[6]Composite powder of hybrid silicone; KSP-100 from Shin-Etsu Chemical Co., Ltd.
[7]In the method as described above, 98 parts by weight of powder was treated with 2 parts by weight of 1/1 mixture of the organopolysiloxane of the Preparation Example 1 and the organopolysiloxane of the Preparation Example 2.

Preparation Procedures

A: Components 7-9, and 15 were mixed, to which components 10-14 were mixed and dispersed in a part of component 20.

B: Components 1 to 6 were mixed.
C: Components 16-18 and the remaining part of component 29 were mixed.
D: While stirring, the mixture obtained in C was added to the mixture obtained in B and emulsified, to which the dispersion obtained in A and component 19 were added.

The water-in-oil type cream foundation thus obtained had a fine texture and was stable with time. It spread lightly on the skin to give moisturized feel. The cosmetic film formed was beautiful, resistant to water and sweat, and durable.

Example 40

Water-in-Oil Type Compact Foundation

| Component | wt % |
|---|---|
| 1. Ceresin | 5.5 |
| 2. Microcrystallin was | 1.0 |
| 3. Neopentylglycol dioctanoate | 8.0 |
| 4. Glyceryl trioctanoate | 4.0 |
| 5. Decamethylpentasiloxane | 6.0 |
| 6. Dimethylpolysiloxane(6 mm$^2$/sec (25° C.)) | 6.0 |
| 7. Crosslinked polyether-modified silicone[1] | 4.0 |
| 8. Branched alkyl/polyether co-modified silicone[2] | 1.2 |
| 9. Sorbitan tetraisostearate | 1.0 |
| 10. Glycerin | 0.5 |
| 11. Titanium oxide treated with organopolysiloxane[3] | 8.5 |
| 12. Iron oxide red treated with organopolysiloxane[3] | 0.4 |
| 13. Iron oxide yellow treated with organopolysiloxane[3] | 1.0 |
| 14. Iron oxide black treated with organopolysiloxane[3] | 0.1 |
| 15. 1,3-butylene glycol | 5.0 |
| 16. Sodium citrate | 0.2 |
| 17. Antiseptics | q.s. |
| 18. Perfume | q.s. |
| 19. Purified water | 47.6 |

[1]Crosslinked polyether-modified silicone; KSG-210 from Shin-Etsu Chemical Co., Ltd.
[2]Branched alkyl/polyether co-modified silicone; KF-6038 from Shin-Etsu Chemical Co., Ltd.
[3]In the method as described above, 98 parts by weight of powder was treated with 2 parts by weight of 1/1 mixture of the organopolysiloxane of the Preparation Example 1 and the organopolysiloxane of the Preparation Example 2.

Preparation Procedures
A: Components 4, 9 and 10 were mixed, to which components 11-14 were mixed and dispersed while heating.
B: Components 1-3, and 5-8 were mixed.
C: Components 15-17 and 19 were mixed and heated.
D: While stirring, the mixture obtained in A was added to the mixture obtained in B and dispersed, to which the mixture obtained in C was added and emulsified. To the emulsion, component 18 was added and poured in a container.

The water-in-oil type compact foundation thus obtained had a fine texture and was stable with time. It spread lightly on the skin to give moisturized feel. The cosmetic film formed was beautiful, resistant to water and sweat, and durable.

Example 41

Water-in-Oil Type Stick Foundation

| Component | wt % |
|---|---|
| 1. Ceresin | 5.5 |
| 2. Stearoyl inulin[1] | 2.0 |
| 3. Neopentylglycol dioctanoate | 8.0 |
| 4. Glyceryl trioctanoate | 5.0 |
| 5. Dimethylpolysiloxane(6 mm$^2$/sec(25° C.)) | 11.5 |
| 6. Crosslinked polyglycerin-modified silicone[2] | 4.0 |
| 7. Branched alkyl/polyether co-modified silicone[3] | 1.5 |
| 8. Powder of spherical polymethylsilsesquioxane[4] | 1.5 |
| 9. Lecithin | 0.2 |
| 10. POE Sorbitan monooleate | 0.3 |
| 11. Titanium oxide treated with organopolysiloxane[5] | 8.5 |
| 12. Iron oxide red treated with organopolysiloxane[5] | 0.4 |
| 13. Iron oxide yellow treated with organopolysiloxane[5] | 1.0 |
| 14. Iron oxide black treated with organopolysiloxane[6] | 0.1 |
| 15. Dipropyleneglycol | 5.0 |
| 16. Sodium citrate | 0.2 |
| 17. Sodium chloride | 0.5 |
| 18. Antiseptics | q.s. |
| 19. Perfume | q.s. |
| 20. Purified water | 44.8 |

[1]Stearoyl inulin; Rheopearl ISK, ex Chiba Seihun Co.
[2]Crosslinked polyglycerin-modified silicone; KSG-710 from Shin-Etsu Chemical Co., Ltd.
[3]Branched alkyl/polyether co-modified silicon; KF-6105 from Shin-Etsu Chemical Co., Ltd.
[4]Powder of spherical polymethylsilsesquioxane; KMP-590 from Shin-Etsu Chemical Co., Ltd.
[5]In the method as described above, 98 parts by weight of powder was treated with 2 parts by weight of 1/1 mixture of the organopolysiloxane of the Preparation Example 1 and the organopolysiloxane of the Preparation Example 2.

Preparation Procreators
A: Components 9, 10 and 15 were mixed, to which components 11-14 were mixed. The mixture obtained was dispersed in a part of component 20 and heated.
B: Components 1-8 were mixed by heating.
C: Components 16-18 and the remaining part of component 20 were mixed and heated.
D: While stirring, the mixture obtained in C was added to the mixture obtained in B and emulsified, to which the mixture obtained in A was added and dispersed. To the dispersion, component 19 was added and poured in a container.

The water-in-oil type stick foundation thus obtained was stable with time. It spread lightly on the skin to give moisturized feel. The cosmetic film formed was beautiful, resistant to water and sweat, and durable.

Example 42

Foundation

| Component | Wt (%) |
|---|---|
| 1. Decamethylcyclopentasiloxane | 27.0 |
| 2. Methylphenylpolysiloxane | 3.0 |
| 3. Glyceryl trioctanoate | 10.0 |
| 4. Branched polyglycerin-modified silicone[1] | 1.0 |
| 5. Polyglyceryl monoisostearate | 3.0 |
| 6. Mixture of powder treated for hydrophobicity[2] | 18.0 |
| 7. Iron oxide red | 1.2 |
| 8. Iron oxide yellow | 2.6 |
| 9. Iron oxide black | 0.2 |
| 10. 1,3-Butylene glycol | 7.0 |
| 11. Sodium chloride | 0.5 |
| 12. Antiseptics | q.s. |
| 13. Perfume | q.s. |
| 14. Purified water | balance |

[1]Branched polyglycerin-modified silicone; KF6104 from Shin-Etsu Chemical Co., Ltd.
[2]Mixture of powder treated for hydrophobicity
a. Fine powder of titanium oxide 8.0
b. Fine powder of zinc oxide 4.0
c. Talc 3.0
d. Mica 3.0

Preparation Procedures

A: Components from a to d were mixed. To the resulting powder mixture was added 1 wt. % of organopolysiloxane (Preparation Example 1/Preparation Example 3=1/1) to heat.

B. Components 1 to 5 were mixed and the resulting mixture was dissolved while heating. Components 6 to 9 were added and then the mixture was dispersed homogeneously.

C. Components 10 to 12 and 14 were mixed. The resulting mixture was added to B and the resulting mixture was emulsified.

D: C was cooled and thereto component 13 was added to obtain foundation.

The foundation thus obtained had a fine texture and stable. It spread lightly on the skin and was comfortable to use. The applied foundation had good finish and stays long.

Example 43

Hair Spray for Brushing

| Component | Wt (%) |
|---|---|
| 1. Isopropyl myristate | 1.0 |
| 2. Stearyltrimethylammonium chloride | 0.05 |
| 3. Zinc oxide fine powder treated with organopolysiloxane[1] | 3.0 |
| 4. Ethanol | 25.0 |
| 5. Perfume | q.s. |
| 6. Blowing agent | balance |

[1] In the method as described above, 98 parts by weight of powder was treated with 2 parts by weight of 1/1 mixture of the organopolysiloxane of the Preparation Example 1 and the organopolysiloxane of the Preparation Example 2.

Preparation Procedures

A: Components 1 to 5 were mixed.
B: A was packed into an aerosol can and then component 6 was packed to obtain brushing agent.

The brushing spray thus obtained was stable with time. It gave glossy, soft and easy to comb hair.

Example 44

Rinse

| Component | Wt (%) |
|---|---|
| 1. Ethylene glycol distearate | 3.0 |
| 2. Cetanol | 2.0 |
| 3. Propylene glycol monostearate | 3.0 |
| 4. Dimethylpolysiloxane (100 mm$^2$/sec (25° C.)) | 3.0 |
| 5. Glycerin monostearate | 4.0 |
| 6. Polyoxyethylene (3) stearate | 4.0 |
| 7. Acetyltrimethylammonium chloride | 5.0 |
| 8. Polyoxyethylene (20) cetyl ether | 2.0 |
| 9. Zinc oxide treaed with organopolysiloxane[1] | 2.0 |
| 10. 1,3-Butylene glycol | 5.0 |
| 11. Antiseptics | q.s. |
| 12. Perfume | q.s. |
| 13. Purified water | balance |

[1] In the method as described above, 98 parts by weight of powder was treated with 2 parts by weight of 1/1 mixture of the organopolysiloxane of the Preparation Example 1 and the organopolysiloxane of the Preparation Example 2.

Preparation Procedures

A: Components 1 to 9 were combined and the resulting mixture was stirred to mix.

B. Components 10, 11 and 13 were mixed while heating.

C: B was added to A to mix and then the resulting mixture was cooled and component 12 was added to obtain rinse.

The rinse thus obtained was stable with time. It gave gloss, smoothness and softness to the hair.

Example 45

No Rinse Shampoo

| Component | Wt (%) |
|---|---|
| 1. Lauric acid amide propyldimethylaminoacetic acid betaine (30%) | 15.0 |
| 2. Sodium polyoxyethylene (3) lauryl ether sulfate (27%) | 4.0 |
| 3. Polyoxyethylene (150) distearate | 0.5 |
| 4. Cationized cellulose (4%) | 0.5 |
| 5. Glycerin | 3.0 |
| 6. Dimethylpolysiloxane (1000,000 mm$^2$/sec (25° C.)) | 1.0 |
| 7. Dimethylpolysiloxane (100 mm$^2$/sec (25° C.)) | 3.0 |
| 8. Mica treated with organopolysiloxane[1] | 2.0 |
| 9. Antiseptics | q.s. |
| 10. Perfume | q.s. |
| 11. Purified water | balance |

[1] In the method as described above, 98 parts by weight of powder was treated with 2 parts by weight of 1/1 mixture of the organopolysiloxane of the Preparation Example 1 and the organopolysiloxane of the Preparation Example 3.

Preparation Procedures

A: Components 1 to 5, 9 and 11 were combined and mixed while heating.

B. Components 6 to 8 were mixed and the resulting mixture was dispersed.

C: B was added to A to mix and then, the resulting mixture was cooled. Component 10 was added to obtain no rinse shampoo.

The no rinse shampoo thus obtained was stable with time. It gave gloss, smoothness, and softness to the hair.

Example 46

Treatment

| Component | Wt (%) |
|---|---|
| 1. Ethylene glycol distearate | 1.0 |
| 2. Liquid paraffin | 10.0 |
| 3. Squalane | 5.0 |
| 4. Stearyl alcohol | 1.5 |
| 5. Dimethylpolysiloxane (10 mm$^2$/sec (25° C.)) | 3.0 |
| 6. Stearic acid | 6.0 |
| 7. Polyoxyethylene (3) stearyl alcohol | 4.5 |
| 8. Polyoxyethylene (150) cetyl alcohol | 2.0 |
| 9. Sericite treated with organopolysiloxane[1] | 1.5 |
| 10. 1,3-Butylene glycol | 6.0 |
| 11. Antiseptics | q.s. |
| 12. Perfume | q.s. |
| 13. Purified water | balance |

[1] In the method as described above, 98 parts by weight of powder was treated with 2 parts by weight of 1/1 mixture of the organopolysiloxane of the Preparation Example 1 and the organopolysiloxane of the Preparation Example 2.

Preparation Procedures

A: Components 1 to 9 were mixed while heating.

B. Components 10, 11, and 13 were mixed and the resulting mixture was dispersed.

C: B was added to A to mix thereof, and then the resulting mixture was cooled. Component 10 was added to obtain treatment.

Treatment thus obtained was stable with time. It gave gloss, smoothness, and softness to the hair.

Example 47

Water-in-Oil Type Antiperspirant

| Component | Wt (%) |
|---|---|
| 1. Crosslinked polyether-modified silicone[1] | 7.0 |
| 2. Decamethylcyclopentasiloxane | 10.0 |
| 3. Glyceryl trioctanoate | 7.0 |
| 4. Dipropylene glycol | 5.0 |
| 5. Sodium citrate | 0.2 |
| 6. Aluminum zirconium tetrachlorohydrate | 18.0 |
| 7. Zinc oxide treated with organopolysiloxane[2] | 5.0 |
| 8. Composite powder of phenyl-modified hybrid silicone[3] | 2.0 |
| 9. Perfume | q.s. |
| 10. Purified water | 45.8 |

[1]Crosslinked polyether-modified silicone; KSG-210 from Shin-Etsu Chemical Co., Ltd.
[2]In the method as described above, 98 parts by weight of powder was treated with 2 parts by weight of 1/1 mixture of the organopolysiloxane of the Preparation Example 1 and the organopolysiloxane of the Preparation Example 2.
[3]Composite powder of fluorine-modified hybrid silicone; KSP-300 from Shin-Etsu Chemical Co., Ltd.

Preparation Procedures

A: Components 1 to 3 were mixed.

B. Components 4 to 10 were mixed.

C: B was added to A and the resulting mixture was mixed to emulsify.

Water-in-oil type antiperspirant thus obtained was stable with time. It gave refreshing feel and kept antiperspirant for a long time.

Example 48

Antiperspirant of Roll-on-Type

| Component | Wt (%) |
|---|---|
| 1. Crosslinked polyether-modified silicone[1] | 20.0 |
| 2. Crosslinked dimethylpolysiloxane[2] | 15.0 |
| 3. Dimethylpolysiloxane (6 mm2/sec (25° C.)) | 10.0 |
| 4. Decamethylcyclopentasiloxane | 30.0 |
| 5. Aluminum/zirconium tetrachlorohydrate | 20.0 |
| 6. Zinc oxide treated with organopolysiloxane[3] | 4.0 |
| 7. Perfume | q.s |

[1]Crosslinked polyether-modified silicone; KSG-210 (from Shin-Etsu Chemical Co., Ltd.)
[2]Crosslinked dimethylpolysiloxane; KSG-15 (from Shin-Etsu Chemical Co., Ltd.)
[3]In the method as described above, 98 parts by weight of powder was treated with 2 parts by weight of 1/1 mixture of the organopolysiloxane of the Preparation Example 1 and the organopolysiloxane of the Preparation Example 2.

Preparation Procedures

A. Components 1 to 4 were mixed.

B. Components 5 to 8 were combined to a and the resulting mixture was dispersed homogeneously.

Antiperspirant of roll-on-type thus obtained was stable with time and spread lightly no the skin to give refreshing feel to the skin. Antiperspirant was kept for a long time.

Example 49

Water-in-Oil Type Suncut Lotion

| Component | wt (%) |
|---|---|
| 1. Crosslinked polyether-modified silicone[1] | 3.0 |
| 2. Crosslinked dimethylpolysiloxane[2] | 2.0 |
| 3. Branched polyether-modified silicone[3] | 1.0 |
| 4. Dimethylpolysiloxane (6 mm2/sec at 25° C.) | 5.0 |
| 5. Decamethylpentasiloxane | 36.0 |
| 6. Isotridecyl isononanate | 4.0 |
| 7. Zinc oxide fine powder treated with organopolysiloxane[4] | 15.0 |
| 8. Titanium oxide fine powder treated with organopolysiloxane (Example 1) | 10.0 |
| 9. Branched polyglycerin-modified silicone[5] | 4.0 |
| 10. Silica | 0.2 |
| 11. Dipropyleneglycol | 2.0 |
| 12. Sodium citrate | 0.2 |
| 13. Sodium chloride | 0.5 |
| 14. Antiseptics | q.s. |
| 15. Perfume | q.s. |
| 16. Purified water | 17.1 |

[1]Crosslinked polyether-modified silicone; KSG-210 from Shin-Etsu Chemical Co., Ltd.
[2]Crosslinked dimethylpolysiloxane; KSG-15 from Shin-Etsu Chemical Co., Ltd.
[3]Branched polyether-modified silicone; KF-6028 from Shin-Etsu Chemical Co., Ltd.
[4]In the method as described above, 98 parts by weight of powder was treated with 2 parts by weight of 1/1 mixture of the organopolysiloxane of the Preparation Example 1 and the organopolysiloxane of the Preparation Example 2.
[5]Branched polyglycerin-modified silicone; KF-6104 from Shin-Etsu Chemical Co., Ltd.

Preparation Procreators

A: Components 7-9 were added to a part of component 5 and dispersed with a beads mill.

B: Components 1-4, 6, 10 and the remaining part of component 5 were mixed.

C: Components 11-14 and 16 were mixed and heated.

D: While stirring, the mixture obtained in C was added to the mixture obtained in B and emulsified, to which the dispersion obtained in A and component 15 was added and stirred.

The water-in-oil type suncut lotion thus obtained was finely dispersed and stable. It spread lightly on the skin to give moisturized feel without oiliness to the skin. The applied lotion did not whiten the skin. It was resistant to sweat and durable to keep UV-protective effect for a long time.

Example 50

Water-in-Oil Type Suncut Cream

| Component | wt (%) |
|---|---|
| 1. Crosslinked polyether-modified silicone[1] | 3.0 |
| 2. Crosslinked dimethylpolysiloxane[2] | 6.0 |
| 3. Branched alkyl/polyether co-modified silicone[3] | 1.0 |
| 4. Neopentylglycol dioctanoate | 9.0 |
| 5. Octyl paramethoxycinnamate | 5.0 |
| 6. Titanium oxide fine powder dispersion[4] | 5.0 |
| 7. Zinc oxide fine powder treated with organopolysiloxane[5] | 18.0 |
| 8. Branched alkyl/polyglycerin co-modified silicone[6] | 1.5 |
| 9. Decamethylpentasiloxane | 10.5 |
| 10. Acrlic silicone resin[7] | 12.0 |
| 11. Silica | 0.2 |

-continued

| Component | wt (%) |
|---|---|
| 12. Pentylene glycol | 7.0 |
| 13. Sodium citrate | 0.2 |
| 14. Sodium chloride | 0.5 |
| 15. Perfume | q.s. |
| 16. Purified water | 21.1 |

[1] Crosslinked polyether-modified silicone; KSG-240 from Shin-Etsu Chemical Co., Ltd.
[2] Crosslinked dimethylpolysiloxane; KSG-15 from Shin-Etsu Chemical Co., Ltd.
[3] Branched alkyl/polyether co-modified silicone; KF-6038 from Shin-Etsu Chemical Co., Ltd.
[4] Titanium oxide fine powder dispersion; SPD-T5 from Shin-Etsu Chemical Co., Ltd.
[5] In the method as described above, 98 parts by weight of powder was treated with 2 parts by weight of 1/1 mixture of the organopolysiloxane of the Preparation Example 1 and the organopolysiloxane of the Preparation Example 2.
[6] Branched alkyl/polyglycerinco-modified silicone; KF-6105 from Shin-Etsu Chemical Co., Ltd.
[7] Acrylic silicone resin; KP-545 from Shin-Etsu Chemical Co., Ltd.

Preparation Procreators

A: Components 8 and 9 were mixed, to which component 7 was added and dispersed with a beads mill.
B: Components 1-5, 10 and 11 were mixed.
C: Components 12-14 and 16 were mixed.
D: The dispersion obtained in A and component 6 were added to the mixture obtained in B, to which the mixture obtained in C was added and emulsified. To the emulsion, component 15 was added and mixed.

The water-in-oil type suncut cream thus obtained was stable with time. It spread lightly on the skin to give refreshing feel to the skin. The applied suncut cream did not whiten the skin. It was resistant to sweat and kept UV-protective effect for a long time.

Example 51

Oil-in-Water Type Suncut Cream

| Component | wt (%) |
|---|---|
| 1. Crosslinked methylphenylpolysiloxane[1] | 5.0 |
| 2. Cetyl isooctanoate | 7.0 |
| 3. Titanium oxide fine powder(Example 1) | 6.0 |
| 4. Decamehtylcyclopentasiloxane | 8.0 |
| 5. Branched polyether-modified silicone[2] | 1.0 |
| 6. Polyether-modified silicone[3] | 1.0 |
| 7. Mixture of acrylamide[4] | 2.0 |
| 8. Propyleneglycol | 5.0 |
| 9. Methyl cellulose(2% aqueous solution)[5] | 5.0 |
| 10. Antiseptics | q.s. |
| 11. Perfume | q.s. |
| 12. Purified water | 60.0 |

[1] Crosslinked methylphenylpolysiloxane; KSG-18 from Shin-Etsu Chemical Co., Ltd.
[2] Branched polyether-modified silicone; KF-6028 from Shin-Etsu Chemical Co., Ltd.
[3] Polyether-modified silicone; KF-6011 from Shin-Etsu Chemical Co., Ltd.
[4] Mixture of acrylamide; SEPIGEL 305 from Seppic Co.
[5] Methyl cellulose; Metholose SM-4000 from Seppic Co.

Preparation Procreators

A: Components 3 to 5 were mixed.
B: Components 1 and 2 were mixed, to which the mixture obtained in A was added and mixed.
C: Components 6 to 10 and 12 were mixed.
D: The mixture obtained in B was added to the mixture obtained in C and emulsified.

The oil-in-water type suncut cream thus obtained had a fine texture and was stable with time. It spread lightly on the skin to give refreshing feel to the skin. The applied suncut cream was resistant to sweat and kept UV-protective effect for a long time.

Example 52

Nonaqueous Emulsion

| Component | wt (%) |
|---|---|
| 1. Crosslinked dimethylpolysiloxane[1] | 30.0 |
| 2. Decamehtylcyclopentasiloxane | 15.0 |
| 3. Dimethylpolysiloxane (6 mm$^2$/sec at 25° C.) | 6.0 |
| 4. Crosslinked polyglycerin-modified silicone[2] | 3.0 |
| 5. Branched alkyl/polyglycerin-modified silicone[3] | 1.0 |
| 6. Dimethyl distearyl ammonium hectlite | 2.0 |
| 7. 1,3-butyleneglycol | 38.0 |
| 8. Sorbitan tetraisostearate | 1.0 |
| 9. Mica coated with titanium treated with organopolysiloxane[4] | 2.0 |

[1] Crosslinked dimethylpolysiloxane; KSG-15 from Shin-Etsu Chemical Co., Ltd.
[2] Crosslinked polyglycerin-modified silicone; KSG-710 from Shin-Etsu Chemical Co., Ltd.
[3] Branched alkyl/polyglycerin-modified silicone; KF-6105 from Shin-Etsu Chemical Co., Ltd.
[4] In the method as described above, 98 parts by weight of powder was treated with 2 parts by weight of 1/1 mixture of the organopolysiloxane of the Preparation Example 1 and the organopolysiloxane of the Preparation Example 2.

Preparation Procreators

A: Components 1 to 6 were mixed.
B: Components 7 to 9 were mixed.
C: The mixture obtained in B was added to the mixture obtained in A and emulsified.

The nonaqueous emulsion thus obtained was stable with time. It spread lightly on the skin to give moisturized feel without oiliness to the skin.

Example 53

W/O/W Type Cream

| Component | wt (%) |
|---|---|
| 1. Crosslinked polyether-modified silicone[1] | 5.0 |
| 2. Cetyl isooctanoate | 5.0 |
| 3. Crosslinked alkyl-modified dimethylpolysiloxane[2] | 1.0 |
| 4. Decamehtylcyclopentasiloxane | 5.0 |
| 5. Methylglucose dioleate | 1.5 |
| 6. Isohexadecane | 3.5 |
| 7. Magnesium sulfate | 0.5 |
| 8. Propylene glycol | 5.0 |
| 9. Purified water | 39.5 |
| 10. Cetyl alcohol | 1.0 |
| 11. PEG-10 soya seterol | 2.0 |
| 12. Mica coated with titanium treated with organopolysiloxane[3] | 0.5 |
| 13. Antiseptics | q.s. |
| 14. Perfume | q.s. |
| 15. Purified water | 30.5 |

[1] Crosslinked polyether-modified silicone; KSG-210 from Shin-Etsu Chemical Co., Ltd.
[2] Crosslinked alkyl-modified dimethylpolysiloxane; KSG-43 from Shin-Etsu Chemical Co., Ltd.
[3] In the method as described above, 98 parts by weight of powder was treated with 2 parts by weight of 1/1 mixture of the organopolysiloxane of the Preparation Example 1 and the organopolysiloxane of the Preparation Example 2.

Preparation Procreators

A: Components 7 to 9 were mixed.
B: Components 1 to 6 were mixed, to which the mixture obtained in A was added and emulsified by stirring.

C: Components 10 to 13, and 15 were mixed, to which the emulsion obtained in B was added and emulsified, while stirring.

D: Component 14 was added to the emulsion obtained in C.

The W/O/W type cream thus obtained was stable with time. It spread lightly on the skin to give refreshing feel. The applied cream had transparent appearance and was resistant to sweat.

Example 54

O/W/O Type Lotion

| Component | wt (%) |
| --- | --- |
| 1. Crosslinked polyether-modified silicone[1] | 3.0 |
| 2. Glyceryl triisooctanoate | 15.0 |
| 3. Crosslinked dimethylpolysiloxane[2] | 5.0 |
| 4. Sucrose monostearate | 3.0 |
| 5. Glycerin | 5.0 |
| 6. 1,3-butylene glycol | 5.0 |
| 7. Sericite treated with organopolysiloxane (Example 3) | 0.5 |
| 8. Antiseptics | q.s. |
| 9. Purified water | 60.0 |
| 10. Macadamia nut oil | 2.0 |
| 11. Cetyl alcohol | 2.0 |
| 12. Perfume | q.s. |

[1] Crosslinked polyether-modified silicone; KSG-210 from Shin-Etsu Chemical Co., Ltd.
[2] Crosslinked dimethylpolysiloxane; KSG-15 from Shin-Etsu Chemical Co., Ltd.

Preparation Procreators

A: Components 1 to 3 were mixed.

B: Components 4 to 9 were mixed and heated.

C: Components 10 and 11 were mixed and heated.

D: While stirring, the mixture obtained in C was added to the mixture obtained in B and emulsified, then cooled.

E: While stirring, the emulsion obtained in D was added to the mixture obtained in A and emulsified further.

The O/W/O type cream thus obtained was stable with time. It spread lightly on the skin to give refreshing feel.

Example 55

O/W/O Type Liquid Foundation

| Component | wt (%) |
| --- | --- |
| 1. Crosslinked alkyl and polyether co-modified silicone[1] | 5.0 |
| 2. Propylene glycol decanoate | 5.0 |
| 3. Isopropyl myristate | 5.0 |
| 4. Titanium oxide treated with organopolysiloxane[2] | 8.5 |
| 5. Alkylsilylated iron oxide[3] | 1.5 |
| 6. Egg yolk origin hydrogenated phosphoLipid | 1.0 |
| 7. Glycerin | 2.0 |
| 8. 1,3-butylene glycol | 10.0 |
| 9. Antiseptics | q.s. |
| 10. Purified water | 52.0 |
| 11. Squalane | 3.0 |
| 12. Crosslinked alkyl-modified dimethylpolysiloxane[4] | 2.0 |
| 13. Cetyl alcohol | 5.0 |
| 14. Perfume | q.s. |

[1] Crosslinked alkyl and polyether co-modified silicone; KSG-310 from Shin-Etsu Chemical Co., Ltd.
[2] In the method as described above, 98 parts by weight of powder was treated with 2 parts by weight of 1/1 mixture of the organopolysiloxane of the Preparation Example 1 and the organopolysiloxane of the Preparation Example 2.
[3] Alkylsilylated iron oxide; AES-3083 treated iron oxide from Shin-Etsu Chemical Co., Ltd.
[4] Crosslinked alkyl-modified dimethylpolysiloxane; KSG-44 from Shin-Etsu Chemical Co., Ltd.

Preparation Procreators

A: Components 1 to 3 were mixed.

B: Components 4 to 10 were mixed and heated.

C: Components 11 to 13 were mixed and heated.

D: While stirring, the mixture obtained in C was added to the mixture obtained in B and emulsified, which was then cooled.

E: While stirring, the emulsion obtained in D was added to the mixture obtained in A and emulsified, to which component 14 was added and mixed.

The O/W/O type liquid foundation thus obtained was stable with time. It spread lightly on the skin to give refreshing feel. The applied foundation had transparent appearance and was durable.

INDUSTRIAL APPLICABILITY

The powder treated with the present surface treatment combination disperses well to give a cosmetic which spread lightly on the skin or the hair. The powder neither evolves hydrogen gas nor changes properties of the cosmetic with time because of significantly reduced surface activity. The applied cosmetic is resistant to sweat and sebum, and stays long.

The invention claimed is:

1. Powder of which surface has been treated with a combination for surface treating powder composed of (I) organopolysiloxane or condensate thereof and (II) organopolysiloxane in a weight ratio of (I):(II) of from 95:5 to 5:95; or (I) organopolysiloxane or condensate thereof, (II) organopolysiloxane, and (III) acryl/silicone copolymer in a weight ratio of (I):[(II)+(III)] of from 95:5 to 5:95, wherein (I) organopolysiloxane is represented by the following formula (1)

$$R^1_a(OR^2)_b SiO_{(4-a-b)/2} \quad (1)$$

wherein $R^1$ may be the same with or different from each other and is a $C_{1-30}$ alkyl, aryl, aralkyl, fluorinated alkyl or amino-substituted alkyl group, $R^2$ is a $C_{1-6}$ alkyl group, a is a number of from 0.75 to 1.5, and b is a number of from 0.2 to 3, provided that a sum of a and b is greater than 0.9 and at most 4;

(II) organopolysiloxane is represented by the formula (2)

$$R^3_c R^4_d R^5_e SiO_{(4-c-d-e)/2} \quad (2)$$

wherein $R^3$ may be the same with or different from each other and is a $C_{1-30}$ alkyl, aryl, aralkyl, or fluorinated alkyl group, and c is a number of from 1.0 to 2.5, $R^4$ is a hydrogen atom, a hydroxyl group or a $C_{1-6}$ alkoxy group and is bonded to the Si atom in the formula (2) via a group comprising carbon, oxygen, or silicon atom, and d is a number of from 0.001 to 1.5, and $R^5$ is a silicone compound residue represented by the following formula (3)

$$-C_xH_{2x}-(SiO)_y-SiR^3_3 \quad (3)$$

with $R^3$ substituents as shown wherein R³ is as defined above, e is a number greater than 0 and up to 1.5, x is an integer of from 1 to 5, and y is an integer of from 0 to 500; and (III) acryl/silicone copolymer having at least one hydrolyzable silyl group.

2. The surface treated powder according to claim 1, wherein the powder is zinc oxide.

3. The surface treated powder according to claim 1, wherein the powder is titanium oxide.

4. The surface treated powder according to claim 1, wherein the powder is selected from the group consisting of mica, sericite, talc and kaolin.

5. A cosmetic comprising the surface treated powder according to claim 1.

6. The cosmetic according to claim 5, wherein the cosmetic further comprises (B) unctuous agent.

7. The cosmetic according to claim 6, wherein at least a part of said unctuous agent (B) is liquid at room temperature.

8. The cosmetic according to claim 6, wherein at least a part of the unctuous agent (B) is a linear, branched or cyclic silicone oil represented by the formula, $R^6_f SiO_{(4-f)/2}$, wherein $R^6$ is a hydrogen, a $C_{1-30}$ alkyl, aryl, aralkyl, or fluorinated alkyl group and f is the number of from 0 to 2.5.

9. The cosmetic according to claim 6, wherein at least a part of said unctuous agent (B) has a fluorine-containing group or an amino group.

10. The cosmetic according to claim 5, wherein the cosmetic further comprises (C) water.

11. The cosmetic according to claim 5, wherein the cosmetic further comprises (D) a compound having an alcoholic hydroxyl group.

12. The cosmetic according to claim 11, wherein the compound having an alcoholic hydroxyl group (D) is at least one selected from the group consisting of water-soluble monohydric alcohols and water-soluble polyhydric alcohols.

13. The cosmetic according to claim 5, wherein the cosmetic further comprises (E) a water-soluble or water-swellable polymer.

14. The cosmetic according to claim 5, wherein the cosmetic further comprises (F) powder.

15. The cosmetic according to claim 14, wherein at least a part of said powder (F) is fine powder of crosslinked dimethylsilicone, fine powder of polymethylsilsesquioxane, or fine powder of hydrophobic silica.

16. The cosmetic according to claim 14, wherein at least a part of said powder (F) has a fluorine-containing group.

17. The cosmetic according to claim 5, wherein the cosmetic further comprises (G) a surfactant.

18. The cosmetic according to claim 17, wherein said surfactant (G) is a linear or branched organopolysiloxane or organopolysiloxane co-modified with polyoxyalkylene and alkyl, each having a polyoxyalkylene moiety or a polyglycerin residue per molecule.

19. The cosmetic according to claim 17, wherein an HLB of said surfactant (G) ranges from 2 to 10.

20. The cosmetic according to claim 5, wherein the cosmetic further comprises (H) a crosslinked organopolysiloxane, except the fine powder of crosslinked dimethylsilicone.

21. The cosmetic according to claim 20, wherein said crosslinked organopolysiloxane (H) is swelled with a silicone oil having a viscosity of from 0.65 mm2/sec to 10.0 mm2/sec at 25° C. in an amount larger than the weight of the crosslinked polyorganosiloxane itself.

22. The cosmetic according to claim 20, wherein said crosslinked organopolysiloxane (H) has a crosslinkage whose both ends are represented by the formula, —CxH2x—, wherein x is an integer of from 2 to 5.

23. The cosmetic according to claim 20, wherein the crosslinkage comprises at least one moiety selected from the group consisting of polyoxyalkylene groups, polyglycerin residues, alkyl groups, alkaline groups, aryl groups, Arlene groups, fluoroalkyl groups, and fluoroalkylene groups.

24. The cosmetic according to claim 5, wherein the cosmetic further comprises (I) a silicone resin, and a crosslinked organopolysiloxane which is not a crosslinked silicone fine powder of crosslinked dimethylsilicone or of polymethylsilsesquioxane, or a hydrophobic silica, or a spherical silicone gum coated with polymethylsilsesquioxane particulates.

25. The cosmetic according to claim 24, wherein said silicone resin (I) is an acrylic silicone resin.

26. The cosmetic according to claim 24, wherein said silicone resin (I) is selected from the group consisting of silicone network resins of MQ type, MDQ type, MT type, MDT type, and MDTQ type.

27. The cosmetic according to claim 25, wherein said silicone resin (I) comprises at least one moiety selected from the group consisting of pyrrolidone residue, long-chain alkyl groups, polyoxyalkylene groups, fluoroalkyl groups, and amino group.

28. The cosmetic according to claim 5, wherein the cosmetic is a skincare cosmetic, makeup cosmetic, hair care cosmetic, antiperspirant cosmetic, or UV-ray protective cosmetic.

29. The cosmetic according to claim 28, wherein the cosmetic is in the form of liquid, emulsion, cream, solid, paste, gel, powder, pressed powder, mousse, spray, stick, or pencil.

\* \* \* \* \*